US010111692B2

(12) United States Patent
Baker et al.

(10) Patent No.: US 10,111,692 B2
(45) Date of Patent: Oct. 30, 2018

(54) DRILL GUIDE SYSTEM AND METHOD

(71) Applicant: Smith & Nephew, Inc., Memphis, TN (US)

(72) Inventors: Charles R. Baker, Lakeland, TN (US); Gene Edward Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 318 days.

(21) Appl. No.: 15/108,959

(22) PCT Filed: Jan. 8, 2015

(86) PCT No.: PCT/US2015/010627
§ 371 (c)(1),
(2) Date: Jun. 29, 2016

(87) PCT Pub. No.: WO2015/105979
PCT Pub. Date: Jul. 16, 2015

(65) Prior Publication Data
US 2016/0324552 A1 Nov. 10, 2016

Related U.S. Application Data

(60) Provisional application No. 61/924,968, filed on Jan. 8, 2014.

(51) Int. Cl.
A61B 17/17 (2006.01)
A61B 17/80 (2006.01)
A61B 17/88 (2006.01)

(52) U.S. Cl.
CPC .......... A61B 17/80 (2013.01); A61B 17/1728 (2013.01); A61B 17/8033 (2013.01);
(Continued)

(58) Field of Classification Search
CPC .............. A61B 17/1728; A61B 17/808; A61B 17/8872
See application file for complete search history.

(56) References Cited

U.S. PATENT DOCUMENTS 7,094,242 B2 * 8/2006 Ralph ................ A61B 17/1728
606/96
7,648,508 B2 1/2010 Lutz et al.
(Continued)

FOREIGN PATENT DOCUMENTS

CN 101588761 A 11/2009
CN 101778604 A 7/2010
(Continued)

OTHER PUBLICATIONS

International Search Report; European Patent Office; International Application No. PCT/US2015/010627; dated Feb. 26, 2015; 4 pages.
(Continued)

Primary Examiner — Nicholas Woodall

(57) ABSTRACT

A drill guide system and method including a bone plate and a guide block removably engaged with the bone plate, and with drill guide passages in the guide block substantially aligned with bone screw openings in the bone plate and each having a conically-shaped inner guide surface. A fixed angle drill guide includes a distal portion selectively positioned within a selected one of the drill guide passages and has a conically-shaped outer guide surface matingly engaged with the conically-shaped inner guide surface of a selected drill guide passage to maintain orientation of the fixed angle drill guide at a predetermined fixed angular orientation. A variable angle drill guide includes a distal portion selectively positioned within a selected one of the drill guide passages and has an outer guide surface sized smaller than the conically-shaped inner guide surface of a selected drill guide
(Continued)

passage to permit orientation of the variable angle drill guide at a variable angular orientation. The drill guide system and method may further include a depth gauge and/or an orthopedic driver instrument.

35 Claims, 12 Drawing Sheets

(52) U.S. Cl.
CPC ...... *A61B 17/8042* (2013.01); *A61B 17/8047* (2013.01); *A61B 17/808* (2013.01); *A61B 17/8872* (2013.01)

(56) References Cited

U.S. PATENT DOCUMENTS

| | | | | |
|---|---|---|---|---|
| 7,740,649 | B2* | 6/2010 | Mosca | A61B 17/1615 606/280 |
| 8,162,950 | B2* | 4/2012 | Digeser | A61B 17/1728 606/96 |
| 8,523,919 | B2 | 9/2013 | Huebner et al. | |
| 8,936,600 | B2* | 1/2015 | Soliman | A61B 17/1728 606/102 |
| 9,204,912 | B2* | 12/2015 | Price | A61B 17/1728 |
| 2006/0155298 | A1 | 7/2006 | Mueller et al. | |
| 2009/0228047 | A1* | 9/2009 | Derouet | A61B 17/1686 606/286 |
| 2011/0106686 | A1 | 5/2011 | Laird | |
| 2011/0224737 | A1 | 9/2011 | Lewis et al. | |
| 2012/0078252 | A1 | 3/2012 | Huebner et al. | |
| 2012/0253347 | A1 | 10/2012 | Murashko, Jr. | |
| 2016/0374738 | A1* | 12/2016 | Smith | A61B 17/725 606/71 |
| 2017/0049493 | A1* | 2/2017 | Gauneau | A61B 17/8872 |

FOREIGN PATENT DOCUMENTS

| | | |
|---|---|---|
| CN | 103269648 A | 8/2013 |
| EP | 2072016 A1 | 6/2009 |
| EP | 2441398 A1 | 4/2012 |
| WO | 2006/069089 A2 | 6/2006 |
| WO | 2007/041638 A1 | 4/2007 |
| WO | 2009/023666 A2 | 2/2015 |

OTHER PUBLICATIONS

Written Opinion of the International Searching Authority; European Patent Office; International Application No. PCT/US2015/010627; dated Feb. 26, 2015; 7 pages.

Chinese Search Report; State Intellectual Property Office of People's Republic of China; Chinese Patent Application No. 201580012741.4; dated Mar. 12, 2018; 5 pages.

Chinese First Office Action; State Intellectual Property Office of People's Republic of China; Chinese Patent Application No. 201580012741.4; dated Mar. 28, 2018; 9 pages.

\* cited by examiner

DRILL GUIDE SYSTEM AND METHOD

CROSS REFERENCE TO RELATED APPLICATIONS

This application is a U.S. National Phase of International PCT Application No. PCT/US2015/010627 filed on Jan. 8, 2015, which claims the benefit of U.S. Provisional Application No. 61/924,968 filed Jan. 8, 2014, the contents of each application incorporated herein by reference in their entirety.

FIELD OF THE INVENTION

The present invention relates generally to drill guides for use in orthopedic surgical procedures, and more particularly but not exclusively relates to a drill guide system and method for guiding a drill and/or placement of bone screws relative to a bone plate using both variable angle and fixed angle placement methods.

BACKGROUND

Bone plate fixation systems for repairing bone fractures are used in a variety of orthopedic applications. These fixation systems include orthopedic bone plates that may be provided in many shapes, sizes and configurations. In cases where a bone is severely comminuted or if bone segments are missing, the use of a bone plate fixation system promotes healing of the fracture by providing a rigid fixation or support structure between the bone and the plate. In some instances, the bone plate fixation system is designed for use in treating a particular type of bone or a specific portion or region of a bone, and may also be provided with specific structures and/or features that facilitate treatment of the bone and provide the necessary support and stabilization to facilitate healing.

One particular type of orthopedic plate commonly used to treat volar plate injuries is a volar distal radius plate which is specifically designed to treat injuries or fractures associated with the distal radius bone. Volar distal radius plates typically require multiple points of bone screw fixation in the metaphyseal region of the distal radius bone at acute and differing angles relative to the plate. Many times, the angular orientation or trajectory of one or more of the bone screws used to attach the plate to the bone is variable, and the particular angular orientations of the bone screws are determined by the surgeon during the surgical procedure based on patient anatomy and fracture patterns. However, some surgeons prefer to place one or more of the bone screws at a fixed angle and at a predetermined angular orientation or trajectory in the plate.

Drill guide systems are sometimes used in association with a bone plate during a surgical procedure to assist the surgeon in drilling multiple holes at diverging and converging orientations or trajectories within the bone for receipt of a corresponding number of bone screws which attach the bone plate to the bone. Existing drill guide systems accommodate for either variable angle or fixed angle bone screw trajectories, but not both. In order to provide the surgeon with the flexibility to place bone screws using both variable angle and fixed angle placement methods, a comprehensive drill guide system is needed to provide this flexibility in an efficient and cost effective manner.

Thus, there remains a need to provide an improved drill guide system and method for guiding a drill and/or placement of bone screws relative to a bone plate using both variable angle and fixed angle placement methods. The present invention satisfies this need and provides other benefits and advantages in a novel and unobvious manner.

SUMMARY

While the actual nature of the invention covered herein can only be determined with reference to the claims appended hereto, certain forms of the invention that are characteristic of the embodiments disclosed herein are described briefly as follows.

In one form of the invention, a drill guide system is provided which generally includes a bone plate, a guide block, a fixed angle drill guide, and a variable angle drill guide. The bone plate has a number of bone screw openings sized to receive a corresponding number of bone screws. The guide block includes at least two drill guide passages extending therethrough, the guide block selectively and removably engaged with the bone plate wherein the drill guide passages are substantially aligned with corresponding ones of the bone screw openings in the bone plate, and each of the drill guide passages has a conically-shaped inner guide surface. The fixed angle drill guide includes a distal portion selectively positioned within a selected one of the drill guide passages in the guide block and has a conically-shaped outer guide surface matingly engaged with the conically-shaped inner guide surface of a selected drill guide passage to maintain orientation of the fixed angle drill guide at a predetermined fixed angular orientation relative to the guide block and the bone plate. The variable angle drill guide includes a distal portion selectively positioned within a selected one of the drill guide passages in the guide block and has an outer guide surface sized smaller than the conically-shaped inner guide surface of a selected drill guide passage to permit orientation of the variable angle drill guide at a variable angular orientation relative to the guide block and the bone plate.

In another form of the invention, a method is provided which includes the steps of providing a bone plate including a number of bone screw openings sized to receive a corresponding number of bone screws, providing a guide block including at least two drill guide passages extending therethrough with each of the drill guide passages having a conically-shaped inner guide surface, selectively and removably engaging the guide block with the bone plate wherein the drill guide passages are substantially aligned with corresponding ones of the bone screw openings, inserting a fixed angle drill guide including a distal portion having a conically-shaped outer guide surface within a selected one of the drill guide passages in the guide block and matingly engaging the conically-shaped outer guide surface with the conically-shaped inner guide surface of the selected drill guide passage to maintain orientation of the fixed angle drill guide at a predetermined fixed angular orientation relative to the guide block and the bone plate, and inserting a variable angle drill guide including a distal portion within a selected one of the drill guide passages in the guide block with the distal portion of the variable angle drill guide having an outer guide surface sized smaller than the conically-shaped inner guide surface of the selected drill guide passage to permit orientation of the variable angle drill guide at a variable angular orientation relative to the guide block and the bone plate.

It is one object of the present invention to provide an improved drill guide system and method for guiding a drill and/or placement of bone screws relative to a bone plate using both variable angle and fixed angle placement methods. Further embodiments, forms, features, aspects, benefits, objects, and advantages of the present invention will become apparent from the detailed description and figures provided herewith.

DESCRIPTION OF THE ILLUSTRATED EMBODIMENTS

Figure 1:
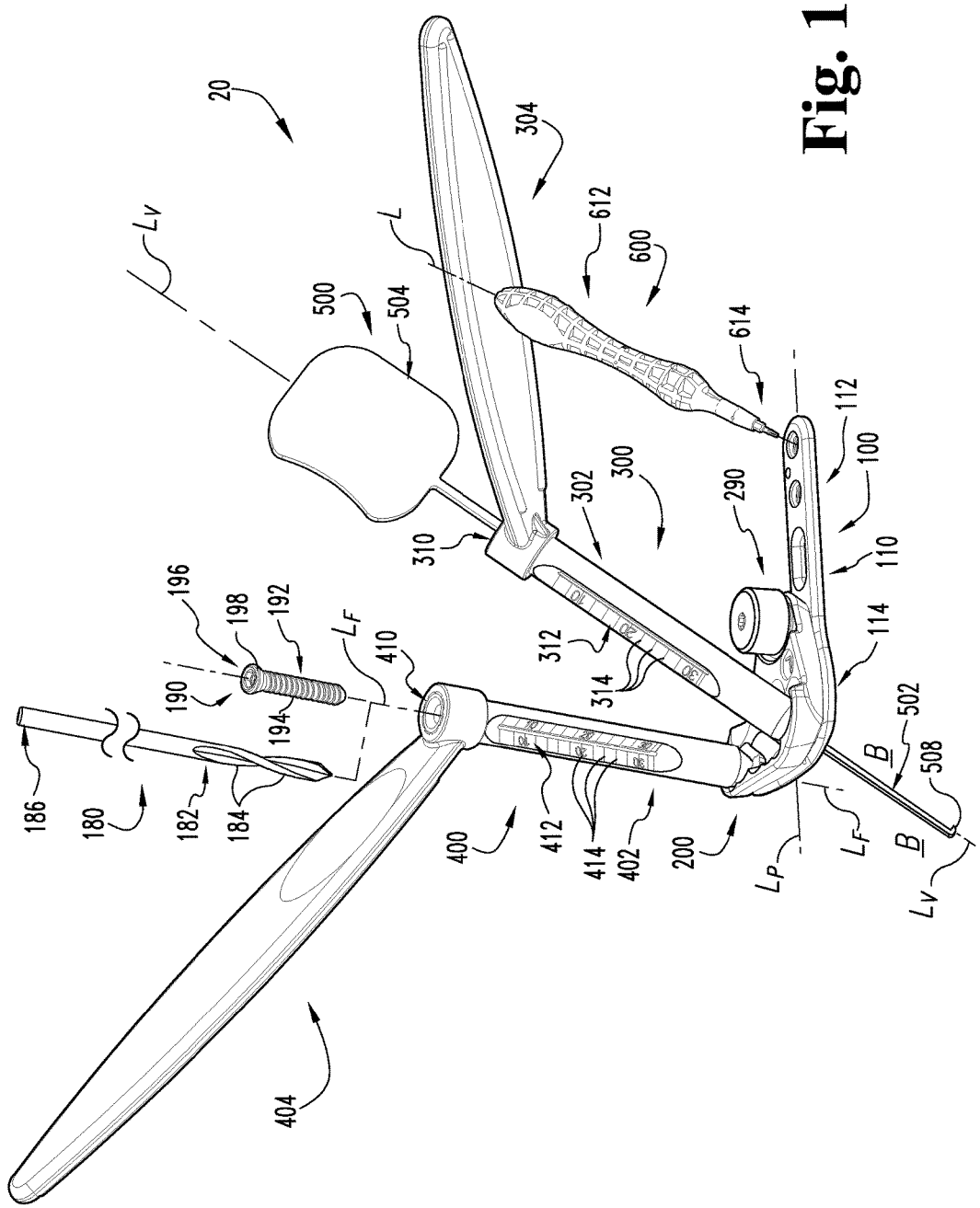
FIG. 1 is a perspective view of a drill guide system according to one form of the present invention.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and uses.

Figure 2:
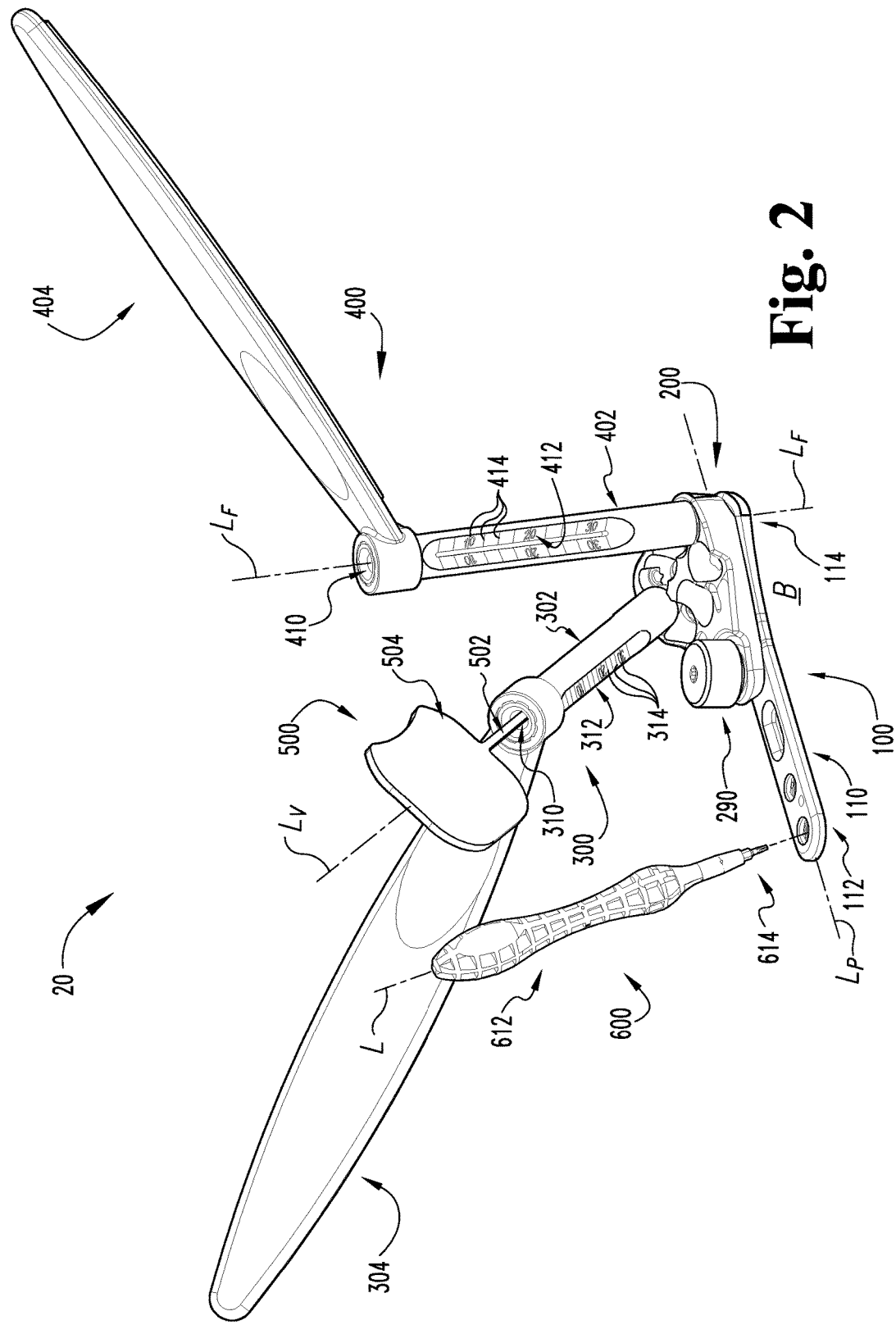
FIG. 2 is another perspective view of the drill guide system of FIG. 1.

Referring to FIGS. 1 and 2, shown therein is a drill guide system 20 according to one form of the present invention. The drill guide system 20 generally includes a bone plate 100 and a number of bone anchors 190 configured to attach the bone plate 100 to a bone B, a guide block 200 and a fastener 290 or other types of engagement mechanisms configured to releasably engage the guide block 200 to the bone plate 100, a variable angle drill guide 300 configured to guide a cutting instrument 180 and/or a bone anchor 190 along a variable longitudinal axis $L_V$, and a fixed angle drill guide 400 configured to guide a cutting instrument 180 and/or a bone anchor 190 along a fixed longitudinal axis $L_F$. The drill guide system 20 may also include a depth gauge 500 configured for use in association with either the variable angle drill guide 300 or the fixed angle drill guide 400 to measure/determine the depth of a bore or opening formed in the bone B and/or to provide an indication as to the proper size/length of the bone anchors 190 to be used for anchoring the bone plate 100 to the underlying bone B. The drill guide system 20 may further include an orthopedic driver instrument 600 configured for driving the bone anchors 190 or other types of bone anchors, screws or fasteners into bone to attach the bone plate 100 to the underlying bone B.

In the illustrated embodiment, the cutting instrument 180 is configured as a drill having a shaft or shank 182 defining flutes 184 or other types of cutting elements adapted to form a bore or opening in bone or bone tissue, and a proximal end portion 186 configured from connection with a rotary power source such as, for example, a motor or another type of rotational driver. However, it should be understood that other types of cutting instruments and other configurations of drills are also contemplated for use in association with the present invention. Additionally, in the illustrated embodiment, the bone anchors 190 are configured as bone screws having a threaded shank portion 192 defining external threads 194 configured for engagement with bone or bone tissue to anchor the bone screw 190 (and the bone plate 100) to the bone B, and a head portion 196 that may be provided with an anti-back out feature 198 such as, for example, an external thread configured for engagement with the bone plate 100 to prevent or inhibit loosening or back-out of the bone screw 190 relative to the bone plate 100 and/or the bone B. The head portion 196 may further include a tool-receiving opening or recess (not shown) sized and configured to receive a distal end of a driver instrument (i.e., driver bit 614 of the driver instrument 600) to facilitate driving of the bone screw 190 into bone. Additionally, the distal end of threaded shank 196 may be fluted or may include another type of cutting element to provide the bone screw 190 with self-tapping or self-drilling capabilities. Although the bone screws 190 are illustrated and described as having a particular size, shape and configuration, it should be appreciated that other sizes, shapes and configurations of bone screws or other types of bone anchors are also contemplated for use in association with the bone plate 100 to secure the bone plate 100 to the underlying bone B.

As will be described in detail below, in one aspect of the invention, the drill guide system 20 is used to guide the drill 180 and/or to position the bone screws 190 relative to the bone plate 100 at angular orientations or trajectories in the underlying bone B using both variable angle and fixed angle placement methods. In one embodiment, the variable angle drill guide 300 is selectively engaged with the guide block 200 in a manner which permits the variable angle drill guide 300 and the variable longitudinal axis $L_V$ to be positioned at variable angular orientations relative to the guide block 200 (and the bone plate 100 and underlying bone B) to permit formation of a bore/opening in the bone B via the drill 180 and/or placement of one of the bone anchors 190 in the bone B within a range of angular orientations or trajectories along the variable longitudinal axis $L_V$. In another embodiment, the fixed angle drill guide 400 is selectively engaged with the guide block 200 in a manner which positions the fixed angle drill guide 400 and the fixed longitudinal axis $L_F$ at a predetermined/predefined fixed angular orientation relative to the guide block 200 (and the bone plate 100 and underlying bone B) to permit formation of a bore/opening in the bone B via the drill 180 and/or placement of one of the bone anchors 190 in the bone B at a fixed angular orientation or trajectory along the fixed longitudinal axis $L_F$. Accordingly, the drill guide system 20 is design and configured to guide the drill 180 and/or to position the bone screws 190 relative to the bone plate 100 at angular orientations or trajectories in the bone B using both variable angle and fixed angle placement methods.

Figure 3:
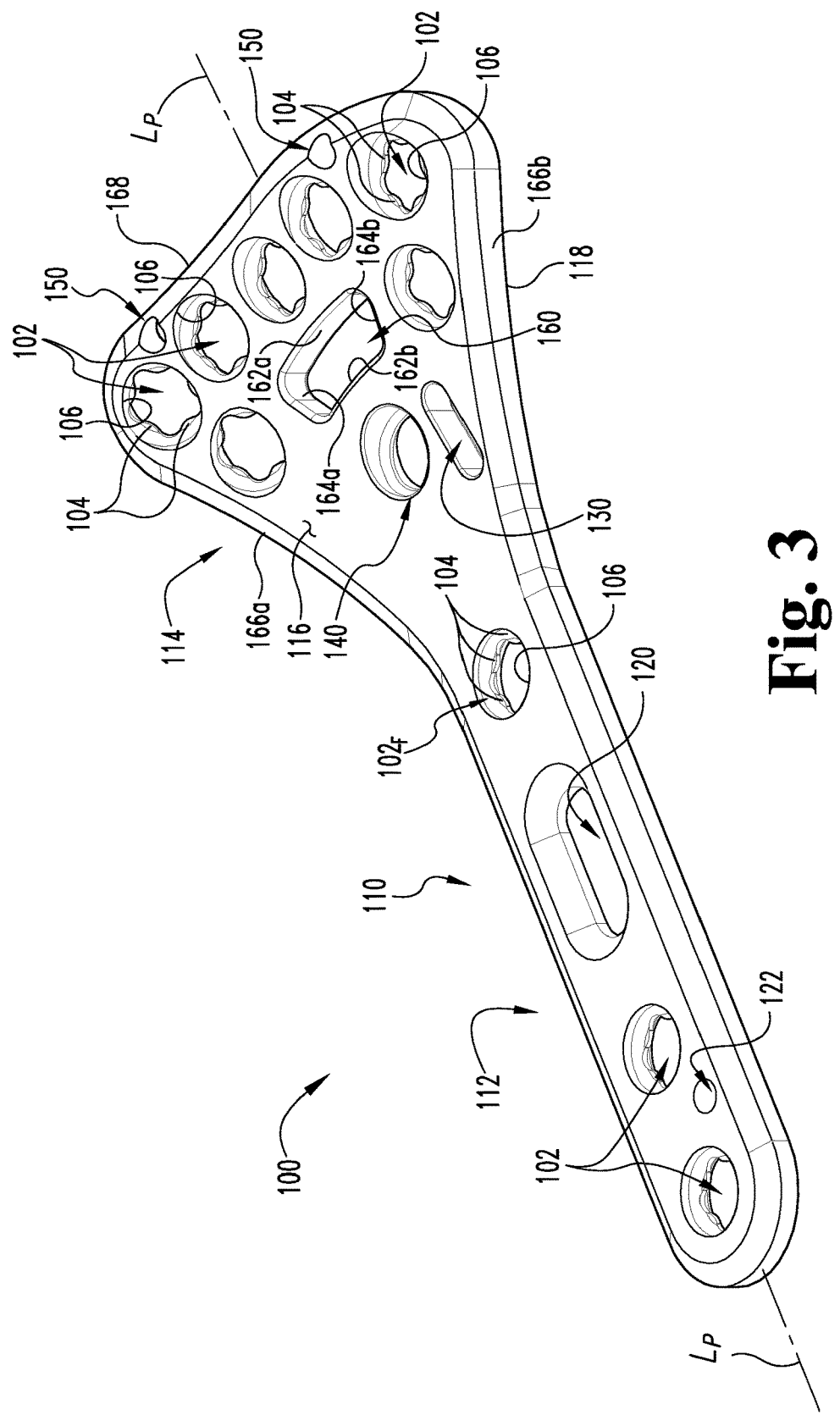
FIG. 3 is a perspective view of one embodiment of a bone plate for use in association with the drill guide system of FIG. 1.

Referring to FIG. 3, in the illustrated embodiment, the bone plate 100 includes a plurality of bone screw openings 102 extending through a thickness of the bone plate 100 and sized to receive the bone screws 190 therein to securely anchor the bone plate 100 to an underlying bone such as, for example, the distal radius bone. In one embodiment, the bone plate 100 is configured for treatment/fixation of fractures, non-unions and osteotomies of the radius bone, and more particularly the distal radius bone. However, it should be appreciated that the bone plate 100 may be configured for use in association with other orthopedic surgeries or procedures associated with other bones, bony structures or joints requiring fixation in addition to the distal radius bone.

At least some of the bone screw openings 102 may include fins or projections 104 that extend radially inward from an inner surface 106 of the bone screw openings 102 and into the interior region of the openings 102, and which are configured to engage or cooperate with the anti-back out feature or external thread 198 formed on the head portion 196 of the bone screw 190 to prevent or inhibit the bone screw 190 from loosening and/or backing out of the bone screw opening 102 in the bone plate 100. The primary purpose of fins 104 is to engage the head portion 196 of the bone screw 190 in order to secure the bone screw 190 at a desired position and at a desired angular orientation within the bone screw opening 102 relative to the bone plate 100. In one embodiment, the bone screw openings 102 are provided with a relatively jagged or undulating inner circumference formed by the inwardly protruding fins 104, and concavities or indentations are formed between adjacent pairs of the fins 104 which extend to a location adjacent the inner surface 106 of the opening 102. Additionally, the fins 104 have a generally round configuration wherein the fins 104 define convex protrusions extending inwardly into the openings 102. The fins 104 may also be provided with a circular shape, a trapezoidal shape, an oval shape, a rectangular shape, a rhomboid shape, a diamond shape, a triangular shape, or other suitable shapes or configurations. In one embodiment, the flexible fins 104 provide each of the bone screw openings 102 with a star-shaped configuration. However, other shapes and configurations of the bone screw openings 102 and/or the flexible fins 104 are also contemplated.

In the illustrated embodiment, the bone plate 100 has a plate body 110 extending along a central longitudinal plate axis $L_P$ and generally including an elongate shaft portion 112 and a triangular-shaped head portion 114 extending from the elongate shaft portion 112. The plate body 110 includes an upper surface 116 facing away from the underlying bone, and a lower bone engaging surface 118 facing the underlying bone. Additionally, the plate body 110 may be formed of any suitable material having appropriate strength, manufacturability, autoclavability, and other desired performance characteristics. Suitable materials include, for example, titanium, stainless steel, cobalt chrome, polyetheretherketone (PEEK), polyethylene, ultra high molecular weight polyethylene (UHMWPE), resorbable polylactic acid (PLA), polyglycolic acid (PGA), combinations or alloys of such materials, or any other appropriate material that has sufficient strength to provide fixation to the underlying bone, while also having sufficient biocompatibility for implantation within the body. Further details regarding the bone plate 100, and more specifically the bone screw opening 102 and the flexible fins 104 are described in commonly-owned U.S. Publication No. 2012/0323284, the contents of which are incorporated herein by reference in their entirety.

In the illustrated embodiment, the elongate shaft portion 112 of the plate body 110 includes a first plurality or grouping of the bone screw openings 102, and may also include an elongate slot 120 having a slot length extending generally along the longitudinal plate axis $L_P$, and a slot width extending across a width of the shaft portion 112 transverse to the longitudinal plate axis $L_P$. As should be appreciated, the elongate slot 120 is sized for receipt of a bone screw which may be displaced along the length of the elongate slot 120 during compression of a bone fracture and prior to terminal/definitive tightening of the bone screw. The elongate shaft portion 112 may also be provided with at least one additional aperture 122 sized for receipt of a pin, an elongate shaft, or a K-wire to provisionally attach the bone plate 100 to the underlying bone prior to anchoring of the bone plate 100 to the bone via the bone screws 190.

Additionally, in the illustrated embodiment, the triangular-shaped head portion 114 of the plate body 110 includes a second plurality or grouping of the bone screw openings 102, and may also include an elongate aperture or slot 130 extending therethrough. In one embodiment, the elongate aperture 130 has an length extending generally along the longitudinal plate axis $L_P$, and an aperture width extending across a width of the triangular-shaped head portion 114 transverse to the longitudinal plate axis $L_P$. In another embodiment, the length of the elongate aperture 130 extends in a direction substantially parallel with the length of the elongate slot 120 in the elongate shaft portion 112. In yet another embodiment, the elongate slot 120 in the elongate shaft portion 112 is centered along the longitudinal plate axis $L_P$, and the elongate aperture 130 in the triangular-shaped head portion 114 is laterally offset from the longitudinal plate axis $L_P$. In still another embodiment, the width of the elongate aperture 130 in the triangular-shaped head portion 114 is less than the width of the elongate slot 120 in the elongate shaft portion 112. In some embodiments, the elongate aperture 130 is sized for receipt of a K-wire or attachment pin extending therethrough and adapted for anchoring in the underlying bone. As should be appreciated, the K-wire or attachment pin may be displaced along the length of the elongate aperture 130 during compression of a bone fracture and prior to secure and terminal engagement of the plate body 110 to the underlying bone.

In a further embodiment, the triangular-shaped head portion 114 may include at least one fastener or bone screw opening 140 extending therethrough that does not include the flexible fins 104 associated with the bone screw openings 102. In another embodiment, the triangular-shaped head portion 114 may include at least one additional pin-receiving aperture 150 sized for receipt of a pin, an elongate shaft, or a K-wire to provisionally attach the plate body 110 to the underlying bone prior to terminal anchoring of the bone plate 100 to the bone via the bone screws 190. In the illustrated embodiment, the triangular-shaped head portion 114 includes a pair of the pin-receiving apertures 150 positioned on opposite sides of the longitudinal plate axis $L_P$ near the distal end surface 168 of the plate body 110.

In yet another embodiment, the triangular-shaped head portion 114 may further include an elongate visualization window 160 extending therethrough. In the illustrated embodiment, the elongate visualization window 160 is generally centered along the longitudinal plate axis $L_P$ and has a shape that is substantially symmetrical relative to the longitudinal plate axis $L_P$. In another embodiment, the elongate visualization window 160 has a window length that extends in a direction transverse to the longitudinal plate axis $L_P$, and preferably in a direction substantially perpendicular to the longitudinal plate axis $L_P$. In still another embodiment, the elongate visualization window 160 has a trapezoidal shape defined by a pair of substantially parallel bases 162a, 162b extending along the window length, and a pair of non-parallel legs 164a, 164b that extend substantially parallel with corresponding peripheral side surfaces 166a, 166b of the triangular-shaped head portion 114 of the plate body 110. However, other shapes and configurations of the visualization window 160 are also contemplated including, for example, a rectangular shape, an oval shape, a diamond shape, or other suitable shapes that provide direct visualization of the underlying bone that would otherwise be covered by the bone plate 100, and more particularly covered by the triangular-shaped head portion 114 of the plate body 110 adjacent the radial head of the distal radius. The elongate visualization window 160 preferably remains unobstructed when the plate body 110 is attached to the underlying bone to provide direct visualization of a portion of the bone located beneath the plate body 110.

Although a particular type and configuration of the bone plate 100 has been illustrated and described, it should be understood that other types and configurations of bone plates are also contemplated. For example, other types and configurations of bone plates are contemplated for use in association with a bone other than the distal radius bone. Additionally, other shapes and configurations of the plate body 110 and/or other shapes, configurations and/or layouts of the bone screw openings 102 are also contemplated for use in association with the present invention. Further details regarding a bone plate and other associated elements suitable for use in association with the present invention are described in commonly-owned U.S. Provisional Application No. 61/920,352, the contents of which are incorporated herein by reference in their entirety.

Figure 4:
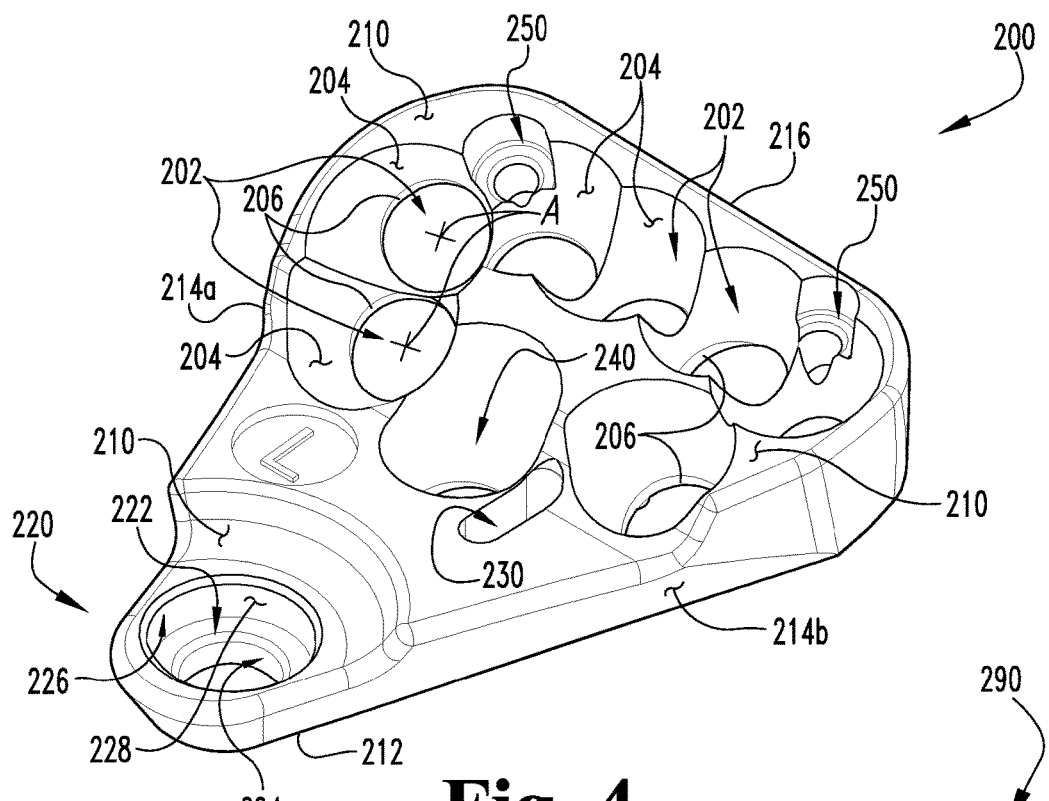
FIG. 4 is a perspective view of one embodiment of a guide block for use in association with the drill guide system of FIG. 1.
Figure 6:
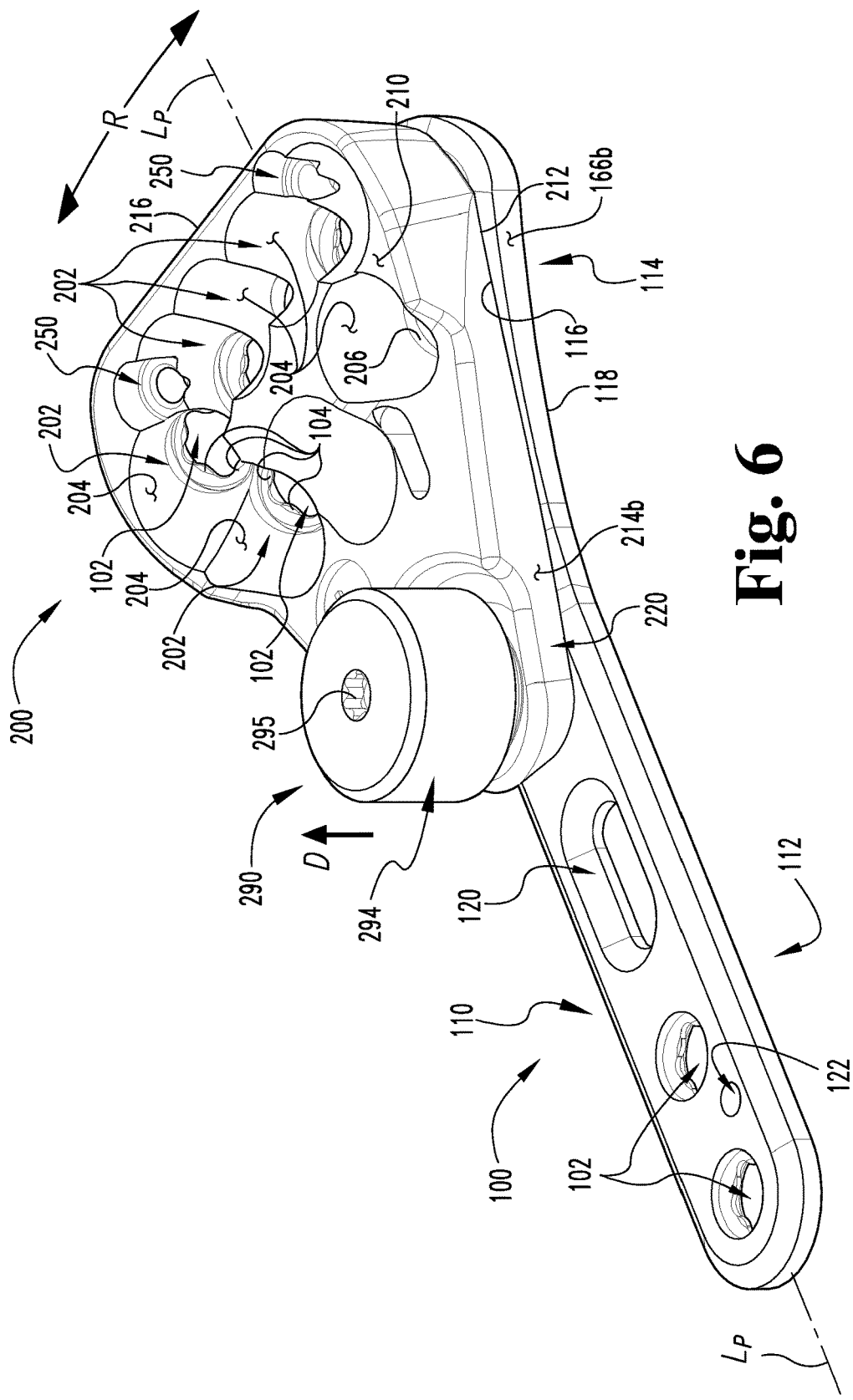
FIG. 6 is a perspective view of the guide block of FIG. 4 temporarily engaged with the bone plate of FIG. 3 by the fastener of FIG. 5.
Figure 8:
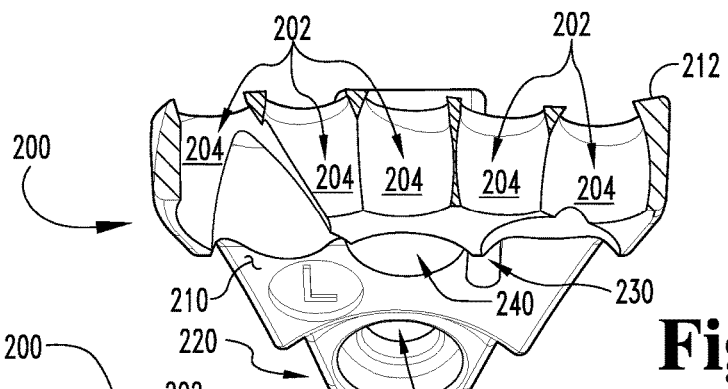
FIG. 8 is a cross-sectional view through the guide block of FIG. 7, as viewed along line 8-8 of FIG. 7.

Referring to FIG. 4, in the illustrated embodiment, the guide block 200 includes multiple drill guide passages 202 extending therethrough, with each of the drill guide passages 202 arranged generally along a passage axis A. As illustrated in FIG. 6, the guide block 200 is selectively and removably engaged with the bone plate 100 by the fastener 290 or another type of engagement element or mechanism wherein the drill guide passages 202 in the guide block 200 are substantially aligned with corresponding ones of the bone screw openings 102 in the head portion 114 of the bone plate 100. In the illustrated embodiment, the guide block 200 includes seven of the drill guide passages 202 that are aligned with seven bone screw openings 102 in the head portion 114 of the bone plate 100. However, it should be appreciated that the guide block 200 may define any number of the drill guide passages 202, including at least two of the drill guide passages 202, and/or the bone plate 100 may define any number of the bone screw openings 102, including at least two of the bone screw openings 102. In other embodiments, the guide block 200 includes at least three of the drill guide passages 202, and the bone plate 100 includes at least three of the bone screw openings 102. Additionally, in the illustrated embodiment, the number of drill guide passages 202 defined by the guide block 200 is equal to the number of bone screw openings 102 defined by the head portion 114 of the bone plate 100. However, it should be understood that the number of drill guide passages 202 in the guide block 200 does not necessarily have to equal the number of bone screw openings 102 in the head portion 114 of the bone plate 100.

In the illustrated embodiment, each of the drill guide passages 202 in the guide block 200 has a conically-shaped inner guide surface 204 that extends along substantially the entire depth of the drill guide passage 202 (i.e., along substantially the entire thickness of the guide block 200). However, in some embodiments, one or more of the drill guide passages 202 may include a cylindrical surface or an outwardly tapering chamfered surface 206 that opens onto the lower plate-engaging surface 212 of the guide block 200. As will be discussed in greater detail below, the drill guide passages 202 and the conically-shaped inner guide surfaces 204 are each shaped and configured to selectively receive and cooperate with the distal end portion of either the variable angle drill guide 300 or the fixed angle drill guide 400. The distal end portion of the variable angle drill guide 300 cooperates with a selected one of the drill guide passages $202_S$ to permit the variable angle drill guide 300 to be positioned at variable angular orientations relative to the guide block 200, which in turn allows for formation of a bore/opening in the underlying bone and/or placement of one of the bone screw 190 within a range of angular orientations or trajectories along the variable longitudinal axis $L_V$. Additionally, the distal end portion of the fixed angle drill guide 400 cooperates with a selected one of the drill guide passages $202_S$ to position the fixed angle drill guide 400 at a fixed angular orientation relative to the guide block 200 to allow formation of a bore/opening in the underlying bone and/or placement of one of the bone screw 190 at a fixed/pre-determined angular orientation or trajectory along the fixed longitudinal axis $L_F$.

Figure 9:
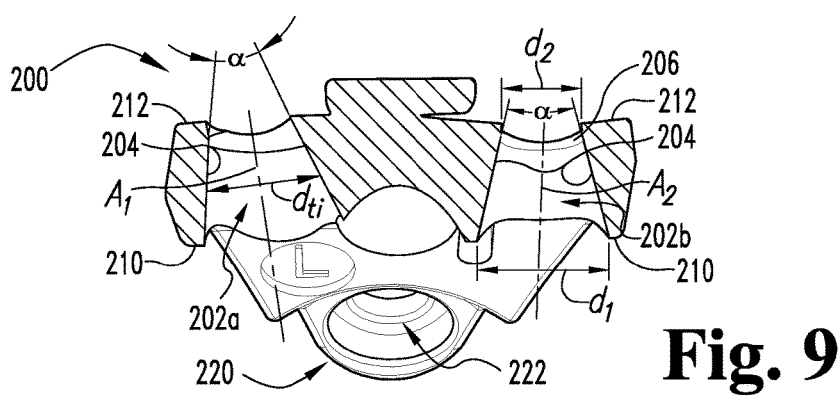
FIG. 9 is a cross-sectional view through the guide block of FIG. 7, as viewed along line 9-9 of FIG. 7.

As indicated above, each of the drill guide passages 202 are arranged generally along a passage axis A. As illustrated in FIG. 9, at least one of the drill guide passages 202a is arranged along a first passage axis $A_1$, and at least one other of the drill guide passages 202b is arranged along a second passage axis $A_2$ that is not parallel (i.e., divergent or convergent) with the first passage axis $A_1$. In other embodiments, at least three of the drill guide passages 202 are arranged along passage axes that are not parallel with one another. Additionally, as illustrated in FIGS. 4 and 6-8, the conically-shaped inner guide surfaces 204 of at least one adjacent pair of the drill guide passages 202 intersect and overlap one another. In some embodiments, the conically-shaped inner guide surfaces 204 of multiple adjacent pairs of the drill guide passages 202 intersect and overlap one another. In other embodiments, the conically-shaped inner guide surface 204 of at least one of the drill guide passages 202 intersects and overlaps the conically-shaped inner guide surface 204 of two other drill guide passages 202. In still other embodiments, the conically-shaped inner guide surface 204 of each of the drill guide passages 202 intersects and overlaps the conically-shaped inner guide surface 204 of at least one other of the drill guide passages 202.

Figure 10:
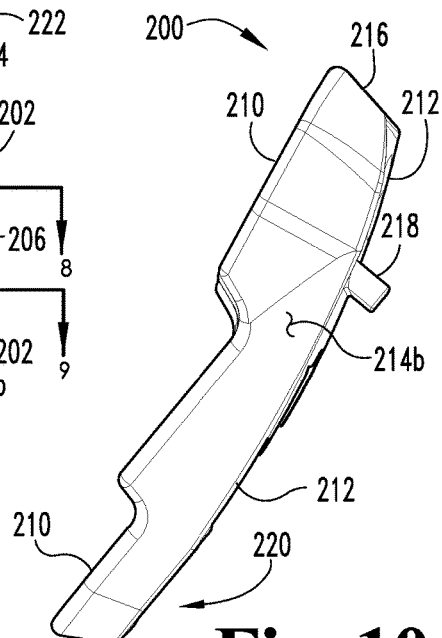
FIG. 10 is a side view of the guide block of FIG. 7.

Additionally, in one embodiment of the invention, the conically-shaped inner guide surface 204 of the drill guide passages 202 defines an acute cone angle α (FIG. 9) between approximately 5 degrees and 60 degrees. In another embodiment, the inner guide surface 204 defines an acute cone angle α between approximately 15 degrees and 45 degrees. In one particular embodiment, the inner guide surface 204 defines an acute cone angle α of approximately 30 degrees. However, it should be appreciated that the conically-shaped inner guide surface 204 may define other acute cone angles α. In the illustrated embodiment, the conically-shaped inner guide surface 204 of the drill guide passages 202 define a cone angle α that inwardly tapers from an upper surface 210 of the guide block 200 (i.e., the block surface facing away from the bone plate 100) to a lower plate-engaging surface 212 of the guide block 200 (i.e., the block surface facing the bone plate 100). In this embodiment, the conically-shaped inner guide surface 204 defines a tapering inner diameter $d_{ti}$ having a first diameter $d_1$ adjacent the upper surface 210 and a smaller second diameter $d_2$ adjacent the lower plate-engaging surface 212. However, other shapes and configurations of the drill guide passages 202 and the conically-shaped inner guide surfaces 204 are also contemplated. Additionally, in the illustrated embodiment, a protrusion or boss 218 (FIG. 10) extends from the lower plate-engaging surface 212 of the guide block 200, the purpose of which will be discussed below.

In the illustrated embodiment, the guide block 200 has an outer perimeter or periphery that generally corresponds to (i.e., substantially complementary) the peripheral size and shape of the triangular-shaped head portion 114 of the bone plate 100. In one embodiment, the guide block 200 and the head portion 114 of the bone plate 100 each have a triangular-shaped peripheral profile. In another embodiment, the guide block 200 includes peripheral side surfaces 214a, 214b that are generally aligned with the peripheral side surfaces 166a, 166b (FIG. 3) of the head portion 114 of the plate body 110 when the guide block 200 is connected to the head portion 114 of the bone plate 100, and a peripheral end surface 216 that is generally aligned with a peripheral end surfaces 168 (FIG. 3) of the head portion 114 of the plate body 110 when the guide block 200 is connected to the head portion 114 of the bone plate 100. In one specific embodiment, the peripheral side surfaces 214a, 214b and the peripheral end surface 216 of the guide block 200 are substantially flat/planar. However, other shapes and configurations of the peripheral side surfaces 214a, 214b and the peripheral end surface 216 are also contemplated including, for example, embodiments where the peripheral side surfaces 214a, 214b and/or the peripheral end surface 216 define convex or concave curvatures. Additionally, in the illustrated embodiment, the lower plate-engaging surface 212 of the guide block 200 (FIG. 10) is shaped and contoured to conform with the upper plate surface 116 of the head portion 114 of the bone plate 100 to provide secure and stable engagement between the guide block 200 and the bone plate 100. In one specific embodiment, the lower plate-engaging surface 212 of the guide block 200 has a convex surface contour (FIG. 10) that generally conforms with a concave surface contour defined by the upper plate surface 116 of the head portion 114 of the bone plate 100. However, other shapes and contours the lower plate-engaging surface 212 of the guide block 200 and the upper plate surface 116 of the bone plate 100 are also contemplated including, for example, flat or multi-angled surfaces.

Figure 7:
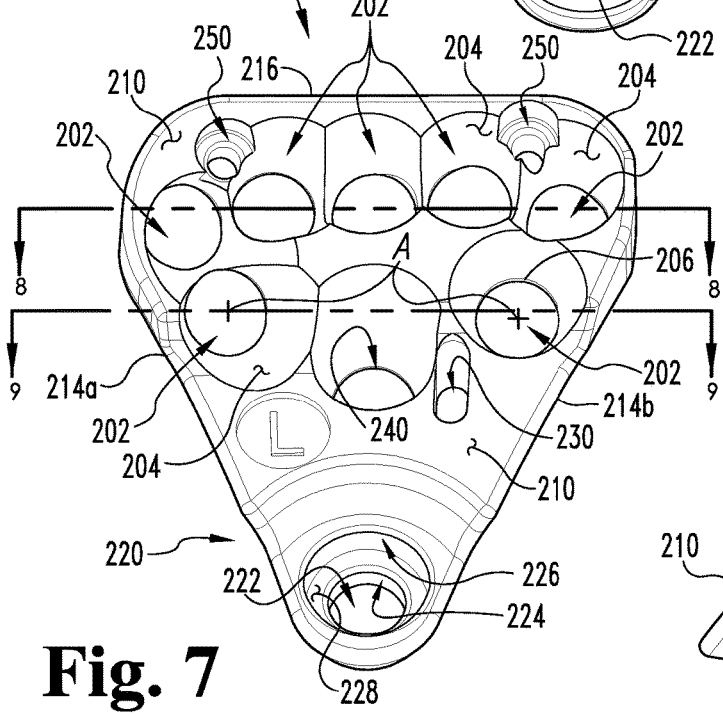
FIG. 7 is a top plan view of the guide block of FIG. 4.

As illustrated in FIGS. 4 and 7, the guide block 200 includes an attachment portion 220 that is configured for selective engagement with the shaft portion 112 of the bone plate 100. In one embodiment, the peripheral side surfaces 214a, 214b of the guide block 200 converge to define the narrow end portion of the triangular-shaped guide block 200, which in turn defines the attachment portion 220. The attachment portion 220 of the guide block 200 defines a fastener opening 222 extending from the upper surface 210 of the guide block 200 to the lower plate-engaging surface 212 and which is sized and shaped to receive a distal portion of the fastener 290 therethrough. The fastener opening 222 includes a lower region 224 that opens onto the lower plate-engaging surface 212 of the guide block 200, and a counter bore region 226 that opens onto the upper surface 210 of the guide block 200, and with the counter bore 226 defining an upwardly-facing shoulder 228. As will be discussed in detail below, the fastener 290 is engaged with the attachment portion 220 of the guide block 200 to removably attach the guide block 200 to the bone plate 100.

Additionally, in the illustrated embodiment, the guide block 200 includes other openings or apertures extending therethrough in addition to the drill guide passages 202. For example, in one embodiment, the guide block 200 includes an elongate slot 230 that is sized and shaped to generally correspond with the elongate slot 130 extending through the head portion 114 of the bone plate 100, and with the elongate slots 130, 230 generally aligned with one another when the guide block 200 is secured to the bone plate 100. In some embodiments, the aligned elongate slots 130, 230 are sized and shaped for receipt of a K-wire or attachment pin adapted for anchoring in the bone. As should be appreciated, the K-wire or attachment pin may be displaced along the length of the aligned slots 130, 230 during compression of a bone fracture and prior to secure and terminal engagement of the plate body 110 to the underlying bone. In a further embodiment, the guide block 200 includes a central passage 240 that is sized and shaped to generally correspond with the fastener opening 140 extending through the head portion 114 of the bone plate 100, with the central passage 240 generally aligned with the fastener opening 140 when the guide block 200 is secured to the bone plate 100. In some embodiments, the central passage 240 and the fastener opening 140 are sized and shaped for receipt of a bone screw, an instrument, a device or an implant therethrough. In still another embodiment, the guide block 200 includes a pair of pin receiving openings 250 that are sized and shaped to generally correspond with the pin receiving openings 150 extending through the head portion 114 of the bone plate 100, with the pin receiving openings 250 generally aligned with the pin receiving openings 150 when the guide block 200 is secured to the bone plate 100. In some embodiments, the aligned pin receiving openings 150, 250 are sized and shaped for receipt of an attachment pin, an elongate shaft, a fastener, or a K-wire that is adapted for anchoring in the bone and which serves to provisionally attach the bone plate 100 (and the guide block 200 connected to the bone plate 100) to the underlying bone prior to terminal anchoring of the bone plate 100 to the bone via the bone screws 190.

Figure 5:
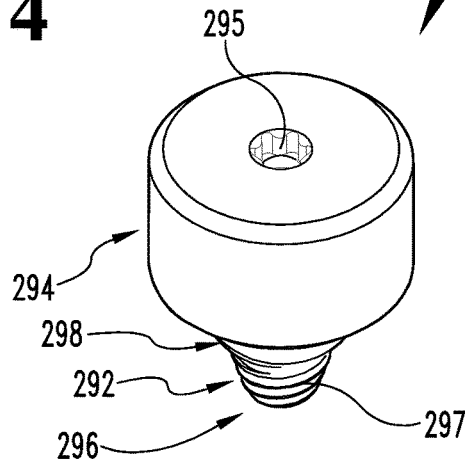
FIG. 5 is a perspective view of one embodiment of a fastener for temporarily engaging the guide block of FIG. 4 with the bone plate of FIG. 3.

Referring to FIG. 5, in the illustrated embodiment, the fastener 290 includes a shaft portion or stem 292 and a head portion or knob 294 positioned atop the shaft portion 292. In one embodiment, the shaft portion 292 includes a distal portion 296 defining one or more engagement elements 297, and a proximal portion 298 defining a relatively smooth cylindrical outer surface. As indicated above, the fastener 290 serves to selectively and removably engage the guide block 200 with the bone plate 100 whereby the drill guide passages 202 in the guide block 200 are substantially aligned with corresponding ones of the bone screw openings 102 in the head portion 114 of the bone plate 100. In one embodiment, the guide block 200 is pre-assembled with the bone plate 100 prior to provisional or terminal attachment of the bone plate 100 to the underlying bone. However, other embodiments are also contemplated wherein the guide block 200 is attached to the bone plate 100 subsequent to attachment of the bone plate 100 to the underlying bone.

In the illustrated embodiment, the distal portion 296 of the fastener 290 extends through the lower region 224 of the fastener opening 222 in the guide block 200 and into the fastener opening $102_F$ defined by the shaft portion 112 of the bone plate 100 (FIG. 3), which in the illustrated embodiment constitutes one of the bone screw openings 102. The engagement element 297 defined by the distal portion 296 cooperates with a corresponding engagement feature of the bone plate 100 to releasably engage the fastener 290 to the bone plate 100, which in turn selectively and removably engages the guide block 200 with the bone plate 100 to prevent disassembly of the guide block 200 from the bone plate 100 in a direction D (FIG. 6) generally perpendicular to the upper surface 116 of the bone plate 100. In the illustrated embodiment, the engagement element 297 defined by the fastener 290 is configured as an external thread or threading that cooperatively engages the fins 104 defined by the fastener opening $102_F$. However, other types and configurations of engagement elements defined by the fastener 290 and the bone plate 100 are also contemplated. The proximal portion 298 of the fastener 290 is positioned within the counter bore 236 of the fastener opening 222 in the guide block 200 to align the fastener 290 relative to the guide block 200, and to provide secure and stable engagement between the fastener 290 and the guide block 200. As should be appreciated, rotational tightening of the fastener 290 compresses the lower surface of the proximal portion 298 of the fastener 290 against the upwardly-facing shoulder 228 defined by the counter bore region 226 to clamp the lower plate-engaging surface 212 of the guide block 200 to the upper plate surface 116 defined by the triangular-shaped head portion 114 of the bone plate 100. The head portion 294 of the fastener 290 may be provided with a tool-receiving opening or recess 295 sized and configured to receive a distal end of a driver instrument (i.e., driver instrument 600) to facilitate rotation of the fastener 290 to tighten the fastener 290 into engagement with the fastener opening $102_F$ in the bone plate 100 to prevent disassembly of the guide block 200 from the bone plate 100 in the direction D.

Additionally, the protrusion or boss 218 (FIG. 10) extending from the lower plate-engaging surface 212 of the guide block 200 is matingly received within a correspondingly shaped opening or recess in the head portion 114 of the bone plate 100 to prevent rotation of the guide block 200 relative to the bone plate 100 in the direction of arrows R (FIG. 6), which in turn maintains the guide block 200 in proper alignment with the head portion 114 of the bone plate 100.

In one embodiment, the protrusion 218 may be matingly received within the elongate visualization window 160 in the head portion 114 to prevent rotation of the guide block 200 in the direction of arrows R. However, it should be understood that the protrusion 218 may be matingly received within other openings or recesses in the bone plate 100 to prevent rotation of the guide block 200 relative to the bone plate 100. Additionally, it should be understood that another feature of the guide block 200 may be engaged with a corresponding feature of the bone plate 100 to prevent rotation of the guide block 200 relative to the bone plate 100. For example, one or more protrusions or shoulders of the guide block 200 may be engaged with a protrusion, shoulder or outer peripheral surface of the bone plate 100, or a protrusion/projection defined by the bone plate 100 may be received within a corresponding opening or recess in the guide block 200.

Although a particular type and configuration of the fastener 290 has been illustrate and described for selectively and removably engaging the guide block 200 to the bone plate 100, it should be understood that other types of fasteners or engagement mechanisms are also contemplated. For example, in another embodiment, the guide block 200 may be connected to the bone plate 100 via a cam mechanism (not shown) that rotates between a locked/engaged position which securely connects the guide block 200 to the bone plate 100, and an unlocked/disengaged position that permits removal/disassembly of the guide block 200 from the bone plate 100. In some embodiments, the cam mechanism would compress the guide block 200 into engagement with the bone plate 100 when transitioned to the locked/engaged position, and may also be configured to compress the bone plate 100 to the underlying bone when transitioned to the locked/engaged position. In still other embodiments, the guide block 200 may be connected to the bone plate 100 via one or more snap features defined by the guide block 200 and/or the bone plate 100, or via a separate fastener that compresses the guide block 200 to the bone plate 100 subsequent to connection via the one or more snap features.

Figures 11, 12:
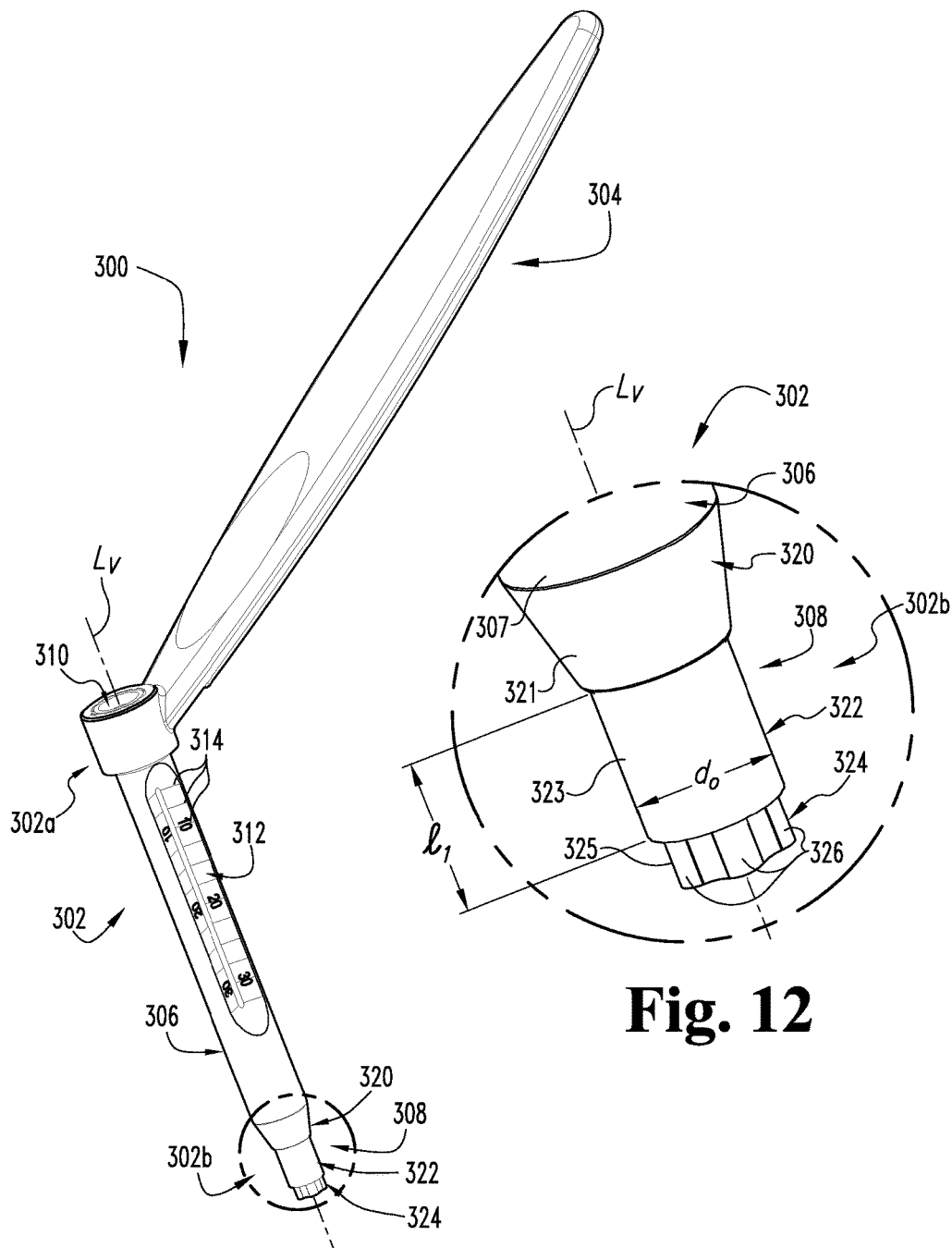
FIG. 11 is a perspective view of one embodiment of a variable angle drill guide for use in association with the drill guide system of FIG. 1.
FIG. 12 is an enlarged perspective view of a distal end portion of the variable angle drill guide of FIG. 11.

Referring to FIGS. 11 and 12, the variable angle drill guide 300 generally includes a tubular guide barrel or guiding portion 302 having a proximal end 302a and a distal end 302b, each arranged generally along a variable longitudinal axis $L_V$, and a handle or gripping portion 304 extending transversely from the guide barrel 302 and configured to be grasped or gripped by a surgeon or other medical personnel to facilitate manipulation and handling of the variable angle drill guide 300. In the illustrated embodiment, the handle 304 extends from the proximal end 302a of the guide barrel 302 in a lateral direction and is arranged at an oblique angle relative to the variable longitudinal axis $L_V$. However, it should be understood that the handle 304 may extend from other portions of the guide barrel 302 and/or may be arranged at any angle relative to the guide barrel 302 including, for example, in a direction normal to the variable longitudinal axis $L_V$. Additionally, although the handle 304 has been illustrated as having a particular shape and configuration, other types and configurations of handles are also contemplated for use in association with the variable angle drill guide 300.

In the illustrated embodiment, the guide barrel 302 includes a generally tubular body or cannula 306 extending along the variable longitudinal axis $L_V$ and having a distal engagement portion 308. As will be discussed in greater detail below, the distal engagement portion 308 is structured and configured to cooperate with a selected one of the drill guide passages 202 in the guide block 200 to permit the variable angle drill guide 300, and more particularly the tubular body 306, to be positioned at variable angular orientations relative to the guide block 200 to allow formation of a bore/opening in the underlying bone and/or placement of a bone anchor within a range of angular orientations or trajectories along the variable longitudinal axis $L_V$. The tubular body 306 defines a longitudinal passage or channel 310 extending along the entire length of the guide barrel 302 from the proximal end 302a to the distal end 302b and arranged along the variable longitudinal axis $L_V$. The longitudinal passage 310 preferably has a circular configuration defining an inner diameter $d_i$ (FIG. 17) along at least a portion of the length of the guide barrel 302 and which is sized in relatively close tolerance with the outer diameter of the shaft 182 of the drill 180 and/or the outer diameter of the bone anchor 190 to thereby guide the drill 180 and/or the bone anchor 190 generally along the variable longitudinal axis $L_V$ and into engagement with the underlying bone.

In another embodiment of the variable angle drill guide 300, the tubular body 306 defines a transverse opening or window 312 extending through a sidewall of the tubular body 306 and into communication with the longitudinal passage 310. In one embodiment, the transverse opening 312 extends through a single side of the tubular body 306. However, in another embodiment, the transverse opening 312 extends through opposite sides of the tubular body 306 (i.e., entirely through the tubular body 306). As should be appreciated, the transverse opening 312 permits direct visualization of instruments or devices inserted into and through the longitudinal passage 310 such as, for example, the drill 180, the bone anchor 190, the depth gauge 500 and/or other devices or instruments that may be used in association with the drill guide system 20.

In a further embodiment of the variable angle drill guide 300, the guide barrel 302 includes indicia markings, graduations, or a scale 314 positioned adjacent the transverse opening 312 and extending along a length of the longitudinal passage 310, the purpose of which will be described below. In one embodiment, the indicia markings or graduations 314 include a series of lines and/or numerals that are indicative of a distance/depth relative to reference location/position. In one embodiment, the indicia markings 314 include a series of lines/markings that are uniformly spaced from one another such as, for example, in two millimeter increments, and also include numerals such as, for example, "10", "20" and "30" which indicate a measured distance relative to a reference location/position. In one specific embodiment, the indicia are indicative of a distance/depth relative to the bottom of a bore/opening formed in the bone underlying the bone plate 100 and the guide block 200. Although one embodiment of the indicia markings or scale 314 has been illustrated and described for use in association with the variable angle drill guide 300, it should be understood that other types and configurations of indicia, markings graduations or scales are also contemplated for use with the drill guide system 20.

In the illustrated embodiment of the variable angle drill guide 300, the distal portion 308 of the guide barrel 302 includes a conical-shaped transition portion 320, a cylindrical-shaped stem portion 322, and a distal-most end portion 324 shaped and configured for engagement within one of the bone screw openings 102 in the bone plate 100. The transition portion 320 includes a conical or angled surface 321 that inwardly tapers from the cylindrical-shaped outer surface 307 of the tubular body 306 to the cylindrical outer surface 323 of the stem portion 322. The cylindrical stem portion 322 extends along an axial length $l_1$ and defines a substantially uniform outer diameter $d_o$. The distal-most end portion 324 extends axially from the cylindrical-shaped stem portion 322 and defines a shaped peripheral outer surface 325 that substantially corresponds to the size and shape of the bone screw openings 102 in the bone plate 100, the purpose of which will be discussed below.

Figure 19:
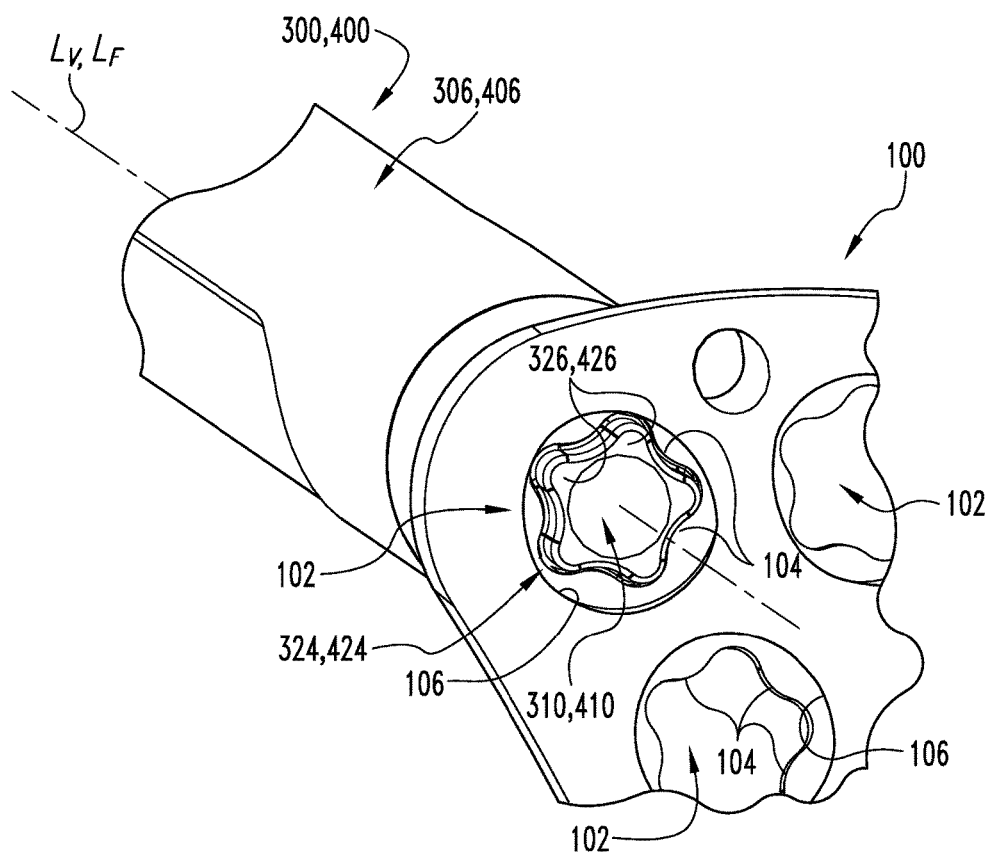
FIG. 19 is a perspective view of a bottom portion of the bone plate of FIG. 3 illustrating a distal-most end portion of the variable angle drill guide of FIGS. 11 and 12 engaged within a selected one of the bone screw openings in the bone plate.

In one specific embodiment, the distal-most end portion 324 has a non-circular shape including a plurality of radially-extending splines or projections 326 extending along an axial length of the distal-most end portion 324 which are sized and shaped for positioning within the recessed regions of the bone screw openings 102 between the flexible fins 104 (FIG. 19). In another specific embodiment, the radially-extending splines 326 provide the peripheral outer surface 325 with a star-shaped configuration that is sized and shaped for receipt within any of the bone screw openings 102 in the bone plate 100 (FIG. 19). Although the distal-most end portion 324 is illustrated and described as having a star-shaped configuration, other shapes and configurations of the distal-most end portion 324 are also contemplated including, for example, a Torx shape, a hexagonal shape, a Phillips shape, a cruciform shape, a square shape, a triangular shape, or other shapes and configuration suitable for receipt within any of the bone screw openings 102 in the bone plate 100.

Figure 17:
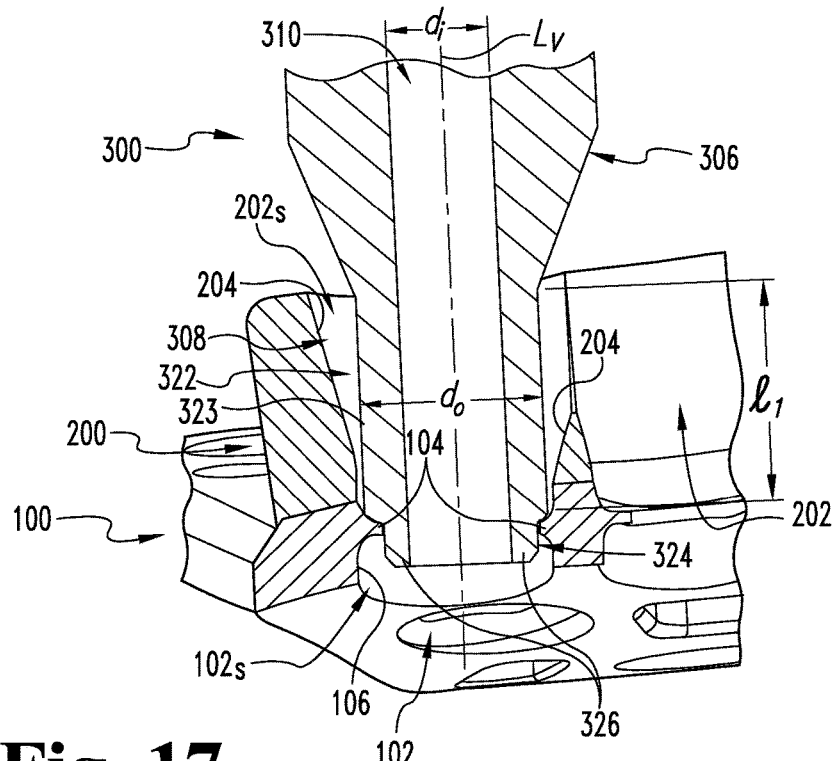
FIG. 17 is a partial cross-sectional view illustrating the distal portion of the variable angle drill guide of FIGS. 11 and 12 engaged within a selected one of the drill guide passages in the guide block of FIG. 4.

Referring to FIG. 17, shown therein is the distal portion 308 of the variable angle drill guide 300 selectively positioned within a selected one 202s of the drill guide passages 202 in the guide block 200, and with the distal-most end portion 324 inserted into the corresponding bone screw openings 102 in the underlying bone plate 100 (i.e., in the bone screw opening 102 aligned with the selected drill guide passage 202s).

As discussed above, the distal-most end portion 324 of the variable angle drill guide 300 and the bone screw openings 102 in the bone plate 100 each have a similar shape and configuration, which in the illustrated embodiment constitutes a star-shaped configuration. As should be appreciated, insertion of the distal-most end portion 324 into the corresponding bone screw opening 102 (i.e., the bone screw opening 102 aligned with the selected drill guide passage 202s) results in mating engagement of the variable angle drill guide 300 with the bone plate 100, and more particularly with the head portion 114 of the bone plate 100. In one embodiment, insertion of the distal-most end portion 324 into the corresponding bone screw opening 102 results in a snap-fit engagement of the variable angle drill guide 300 with the bone plate 100. The snap-fit engagement provides tactile feedback to the surgeon that is indicative of successful and secure engagement between the distal-most end portion 324 and the corresponding bone screw opening 102, as well as proper axial positioning of the drill guide 300 relative to the bone plate 100 and the guide block 200. The snap-fit mating engagement of the distal-most end portion 324 of the drill guide 300 and the corresponding bone screw opening 102 is at least partially attributable to the flexible nature of the fins 104 extending into the bone screw opening 102, as well as the flexible and elastic interaction between the distal-most end portion 324 and the fins 104. Additionally, the mating engagement between the distal-most end portion 324 and the corresponding bone screw opening 102 provides secure and stable engagement between the variable angle drill guide 300 and the bone plate 100 to maintain the variable angle drill guide 300 in a proper axial position and/or angular orientation relative to the bone plate 100 during the formation of the bore/channel in the underlying bone and/or during insertion of the bone anchor 190 into the bone. However, the mating engagement between the distal-most end portion 324 and the corresponding bone screw opening 102 still permits the variable angle drill guide 300 to be angularly displaced and positioned within a range of angular orientations relative to the bone plate 100 and the guide block 200.

As indicated above, the distal portion 308 of the variable angle drill guide 300 may be positioned within any of the drill guide passages 202 in the guide block 200, and may also be positioned within the central passage 240 in the guide block 200. Additionally, the distal portion 308 of the variable angle drill guide 300 is selectively positioned within a select one of drill guide passages 202s in a manner which permits the variable angle drill guide 300 and the variable longitudinal axis $L_V$ to be positioned within a range of angular orientations relative to the guide block 200 (and relative to the aligned bone screw opening 102 in the bone plate 100) to permit formation of a bore/opening in the underlying bone via the drill 180 and/or placement of one of the bone anchors 190 within a range of angular orientations or trajectories along the variable longitudinal axis $L_V$. As illustrated in FIG. 17, when the distal-most end portion 324 of the drill guide 300 is inserted into the aligned bone screw opening 102 in the bone plate 100, the axial length $l_1$ of the cylindrical stem portion 322 extends along the entire depth of the selected drill guide passage 202s in the guide block 202 (i.e., the axial length $l_1$ of the cylindrical stem portion 322 extends at least the thickness of the guide block 200 adjacent the drill guide passage 202s). In this manner, other portions of the drill guide 300 such as, for example, the tubular body 306 and/or the conical-shaped transition portion 320 will not interfere with or otherwise prevent the variable angle drill guide 300 to be positioned within the full range of angular orientations relative to the guide block 200. Additionally, the outer diameter $d_o$ of the cylindrical stem portion 322 is sized somewhat smaller than the minimum inner diameter $d_2$ of the conically-shaped inner guide surface 204 of the selected drill guide passage 202s (i.e., the minimum diameter of the tapering inner diameter $d_{ti}$ of the conical guide surface 204 adjacent the lower plate-engaging surface 212 of the guide block 200).

In this manner, the variable angle drill guide 300 (and more specifically the guide barrel 302) may be positioned at variable angular orientations within the selected drill guide passage 202s until the cylindrical outer surface 323 of the stem portion 322 abuts the conically-shaped inner guide surface 204 of the selected drill guide passage 202s. In one embodiment, the variable angle drill guide 300 may be positioned at variable angular orientations within the selected drill guide passage 202s within the cone angle α defined by the inner guide surface 204 of the selected drill guide passage 202s. As indicated above, in one specific embodiment, the cone angle α defined by the inner guide surface 204 is approximately 30 degrees, which permits the guide barrel 302 and the variable longitudinal axis $L_V$ of the variable angle drill guide 300 to be positioned at any angular orientation within a 30 degree cone of travel. However, as also indicate above, a cone angle α of 30 degrees is exemplary, and other cone angles α are also contemplated.

Once the guide barrel 302 of the drill guide 300 is positioned at a selected angular orientation within the drill guide passage 202s and the variable longitudinal axis $L_V$ is positioned at the appropriate angular orientation, the drill 180 or another type of cutting instrument may be passed through the longitudinal passage 310 and through the aligned bone screw opening 102 in the bone plate 100 to form a bore/opening in the underlying bone along the variable longitudinal axis $L_V$, and/or one of the bone anchors 190 may be passed through the longitudinal passage 310 and through the aligned bone screw opening 102 to anchor the bone anchor in the underlying bone at an angular orientation or trajectory along the variable longitudinal axis $L_V$. As should be appreciated, once the bore/opening is formed in the underlying bone and/or the bone anchor is anchored within the underlying bone, the variable angle drill guide 300 may be removed via disengagement of the distal-most end portion 324 from the bone screw openings 102 in the bone plate 100 and removal of the distal portion 308 of the drill guide 300 from the selected drill guide passage 202s. The variable angle drill guide 300 may then be used in association with another of the drill guide passages 202 to form another bore/opening in the underlying bone at a variable angle and/or to anchor another of the bone anchors 190 within the bone at a variable angle. Alternatively, the fixed angle drill guide 400 may be used in association with another of the drill guide passages 202 to form another bore/opening in the underlying bone at a fixed angle and/or to anchor another of the bone anchors 190 within the bone at a fixed angle, or the guide block 200 may be removed from the bone plate 100 via loosening or unlocking the fastener 290 to permit disengagement of the guide block 200 from the bone plate 100.

Figures 13, 14:
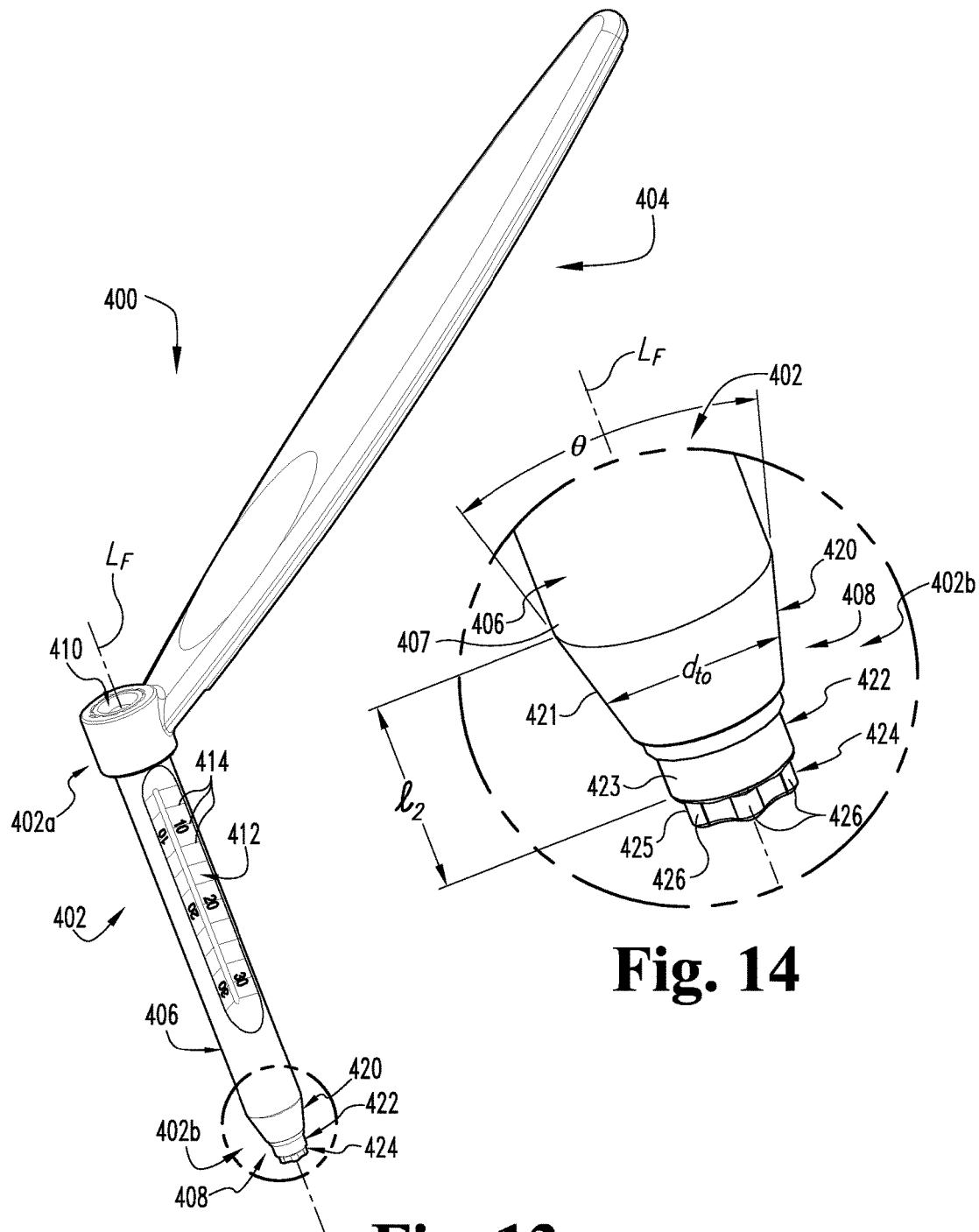
FIG. 13 is a perspective view of one embodiment of a fixed angle drill guide for use in association with the drill guide system of FIG. 1.
FIG. 14 is an enlarged perspective view of a distal end portion of the fixed angle drill guide of FIG. 13.

Referring to FIGS. 13 and 14, the fixed angle drill guide 400 generally includes a tubular guide barrel or guiding portion 402 having a proximal end 402a and a distal end 402b, each arranged generally along a fixed longitudinal axis $L_F$, and a handle or gripping portion 404 extending transversely from the guide barrel 402 and configured to be grasped or gripped by a surgeon or other medical personnel to facilitate manipulation and handling of the fixed angle drill guide 400. In the illustrated embodiment, the handle 404 extends from the proximal end 402a of the guide barrel 402 in a lateral direction and is arranged at an oblique angle relative to the fixed longitudinal axis $L_F$. However, it should be understood that the handle 404 may extend from other portions of the guide barrel 402 and/or may be arranged at any angle relative to the guide barrel 402 including, for example, in a direction normal to the fixed longitudinal axis $L_F$. Additionally, although the handle 404 has been illustrated as having a particular shape and configuration, other types and configurations of handles are also contemplated for use in association with the fixed angle drill guide 400.

In the illustrated embodiment, the guide barrel 402 includes a generally tubular body or cannula 406 extending along the fixed longitudinal axis $L_F$ and having a distal engagement portion 408. As will be discussed in greater detail below, the distal engagement portion 408 is structured and configured to cooperate with a selected one of the drill guide passages 202 in the guide block 200 to position the fixed angle drill guide 400, and more particularly the tubular body 406, at a predetermined/predefined/fixed angular orientation relative to the guide block 200 to allow formation of a bore/opening in the underlying bone and/or placement of a bone anchor at a predetermined/predefined/fixed angular orientation or trajectory along the fixed longitudinal axis $L_F$. The tubular body 406 defines a longitudinal passage or channel 410 extending along the entire length of the guide barrel 402 from the proximal end 402a to the distal end 402b and arranged along the fixed longitudinal axis $L_F$. The longitudinal passage 410 preferably has a circular configuration defining an inner diameter $d_i$ (FIG. 18) along at least a portion of the length of the guide barrel 402, and which is preferably sized in relatively close tolerance with the outer diameter of the shaft 182 of the drill 180 and/or the outer diameter of the bone anchor 190 to thereby guide the drill 180 and/or the bone anchor 190 generally along the fixed longitudinal axis $L_F$ and into engagement with the underlying bone. In one embodiment, the inner diameter $d_i$ of the longitudinal passage 410 in the fixed angle drill guide 400 is substantially equal to the inner diameter $d_i$ of the longitudinal passage 310 in the variable angle drill guide 300 to permit use of both of the drill guides 300, 400 with the same drill 180 and/or bone anchors 190. However, other embodiments are also contemplated wherein the inner diameters $d_i$ of the longitudinal passages 310, 410 in the drill guides 300, 400 can be sized differently from one another.

In another embodiment of the fixed angle drill guide 400, the tubular body 406 defines a transverse opening or window 412 extending through a sidewall of the tubular body 406 and into communication with the longitudinal passage 410. In one embodiment, the transverse opening 412 extends through a single side of the tubular body 406. However, in another embodiment, the transverse opening 412 extends through opposite sides of the tubular body 406 (i.e., entirely through the tubular body 406). As should be appreciated, the transverse opening 412 permits direct visualization of instruments or devices inserted into and through the longitudinal passage 410 such as, for example, the drill 180, the bone anchor 190, the depth gauge 500 and/or other devices or instruments that may be used in association with the drill guide system 20.

In a further embodiment of the fixed angle drill guide 400, the guide barrel 402 includes indicia markings, graduations, or a scale 414 positioned adjacent the transverse opening 412 and extending along a length of the longitudinal passage 410, the purpose of which will be described below. In one embodiment, the indicia markings or graduations 414 include a series of lines and/or numerals that are indicative of a distance/depth relative to reference location/position. In one embodiment, the indicia markings 414 include a series of lines/markings that are uniformly spaced from one another such as, for example, in two millimeter increments, and also include numerals such as, for example, "10", "20" and "30" which indicate a measured distance relative to a reference location/position. In one specific embodiment, the indicia are indicative of a distance/depth relative to the bottom of a bore or channel formed in the bone underlying the bone plate 100 and the guide block 200. Although one embodiment of the indicia markings or scale 414 has been illustrated and described for use in association with the fixed angle drill guide 400, it should be understood that other types and configurations of indicia, markings, graduations or scales are also contemplated for use with the drill guide system 20.

In the illustrated embodiment of the fixed angle drill guide 400, the distal portion 408 of the guide barrel 402 includes a conical-shaped alignment portion 420, a cylindrical-shaped stem portion 422, and a distal-most end portion 424 shaped and configured for engagement within one of the bone screw openings 102 in the bone plate 100. The conical-shaped alignment portion 420 includes a conical or angled alignment surface 421 that inwardly tapers from the cylindrical-shaped outer surface 407 of the tubular body 406 to the cylindrical outer surface 423 of the stem portion 422. The conical alignment surface 421 defines an inwardly tapering or varying outer diameter $d_{to}$ that varies in a substantially uniform manner from the cylindrical-shaped outer surface 407 of the tubular body 406 to the circular-cylindrical outer surface 423 of the stem portion 422.

In one specific embodiment, the conical alignment surface 421 defines an acute cone angle θ that substantially corresponds to the acute cone angle α of the conically-shaped inner guide surface 204 of the drill guide passages 202, the purpose of which will be discussed below. In another specific embodiment, the tapering outer diameter $d_{to}$ of the conical alignment surface 421 substantially corresponds to the tapering inner diameter $d_{ti}$ of the conically-shaped inner guide surface 204 of the drill guide passages 202, the purpose of which will also be discussed below. In yet another specific embodiment, the acute cone angle θ of the conical alignment surface 421 is between approximately 5 degrees and 60 degrees. In a further specific embodiment, the acute cone angle θ is between approximately 15 degrees and 45 degrees. In one particular embodiment, the acute cone angle θ is approximately 30 degrees. However, it should be appreciated that the conical alignment surface 421 may define other acute cone angles θ. In the illustrated embodiment, the conical alignment surface 421 of the conically-shaped alignment portion 420 defines an acute cone angle θ that inwardly tapers from the cylindrical-shaped outer surface 407 of the tubular body 406 to the circular-cylindrical outer surface 423 of the stem portion 422. However, other shapes and configurations of the conical alignment surface 421 and the conically-shaped alignment portion 420 are also contemplated. Additionally, the conical-shaped alignment portion 420 and the cylindrical-shaped stem portion 422 together extend along an axial length $l_2$. The distal-most end portion 424 extends axially from the cylindrical-shaped stem portion 422 and defines a shaped peripheral outer surface 425 that substantially corresponds to the size and shape of the bone screw openings 102 in the bone plate 100, the purpose of which will be discussed below.

In one specific embodiment, the distal-most end portion 424 has a non-circular shape including a plurality of radially-extending splines or projections 426 extending along an axial length of the distal-most end portion 424 which are sized and shaped for positioning within the recessed regions of the bone screw openings 102 between the flexible fins 104. In another specific embodiment, the radially-extending splines 426 provide the peripheral outer surface 425 with a star-shaped configuration that is sized and shaped for receipt within any of the bone screw openings 102 in the bone plate 100. Although the distal-most end portion 424 is illustrated and described as having a star-shaped configuration, other shapes and configurations of the distal-most end portion 424 are also contemplated including, for example, a Torx shape, a hexagonal shape, a Phillips shape, a cruciform shape, a square shape, a triangular shape, or other shapes and configuration suitable for receipt within any of the bone screw openings 102 in the bone plate 100.

Figure 18:
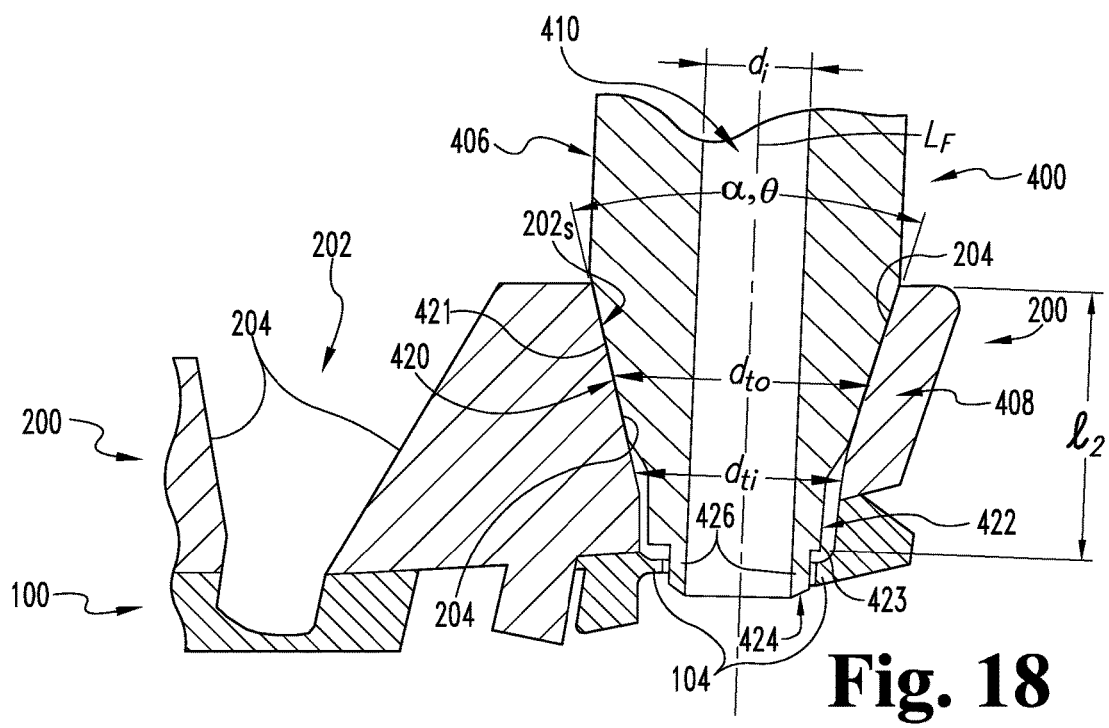
FIG. 18 is a partial cross-sectional view illustrating the distal portion of the fixed angle drill guide of FIGS. 13 and 14 engaged within a selected one of the drill guide passages in the guide block of FIG. 4.

Referring to FIG. 18, shown therein is the distal portion 408 of the fixed angle drill guide 400 selectively positioned within a selected one 202s of the drill guide passages 202 in the guide block 200, and with the distal-most end portion 424 inserted into the corresponding bone screw openings 102 in the underlying bone plate 100 (i.e., in the bone screw opening 102 aligned with the selected drill guide passage 202s).

As discussed above, the distal-most end portion 424 of the fixed angle drill guide 400 and the bone screw openings 102 in the bone plate 100 each have a similar shape and configuration, which in the illustrated embodiment constitutes a star-shaped configuration. As should be appreciated, insertion of the distal-most end portion 424 into the corresponding bone screw opening 102 (i.e., the bone screw opening 102 aligned with the selected drill guide passage 202s) results in mating engagement of the fixed angle drill guide 400 with the bone plate 100, and more particularly the head portion 114 of the bone plate 100. Such mating engagement has been illustrated in FIG. 18 and described above in association with the variable angle drill guide 300, which description and illustration is also applicable with regard to the fixed angle drill guide 400. In one embodiment, insertion of the distal-most end portion 424 into the corresponding bone screw opening 102 results in a snap-fit engagement of the fixed angle drill guide 400 with the bone plate 100. The snap-fit engagement provides tactile feedback to the surgeon that is indicative of successful and secure engagement between the distal-most end portion 424 and the corresponding bone screw opening 102, as well as proper axial positioning of the drill guide 400 relative to the bone plate 100 and the guide block 200. The snap-fit mating engagement of the distal-most end portion 424 of the drill guide 400 and the corresponding bone screw opening 102 is at least partially attributable to the flexible nature of the fins 104 extending into the bone screw opening 102, as well as the flexible and elastic interaction between the distal-most end portion 424 and the fins 104. Additionally, the mating engagement between the distal-most end portion 424 and the corresponding bone screw opening 102 provides secure and stable engagement between the fixed angle drill guide 400 and the bone plate 100 to maintain the drill guide 400 in a proper axial position relative to the bone plate 100 during the formation of the bore/channel in the underlying bone and/or during insertion of the bone anchor 190 into the underlying bone.

As indicated above, the distal portion 408 of the fixed angle drill guide 400 may be positioned within any of the drill guide passages 202 in the guide block 200, and is selectively positioned within a select one of drill guide passages 202s in a manner which positions and maintains the fixed angle drill guide 400 and the fixed longitudinal axis $L_F$ at a predetermined/predefined angular orientation relative to the guide block 200 (and relative to the aligned bone screw opening 102 in the bone plate 100) to permit formation of a bore/opening in the underlying bone via the drill 180 and/or placement of one of the bone anchors 190 at a single predetermined/predefined angular orientation or trajectory along the fixed longitudinal axis $L_F$.

As illustrated in FIG. 18, when the distal-most end portion 424 of the drill guide 400 is inserted into the aligned bone screw opening 102 in the bone plate 100, the axial length $l_2$ defined by the conical-shaped alignment portion 420 and the cylindrical-shaped stem portion 422 extends along substantially the entire depth of the selected drill guide passage 202s in the guide block 202 (i.e., the axial length $l_2$ extends along substantially the entire thickness of the guide block 200 adjacent the selected drill guide passage 202s). In this manner, the distal portion 408 of the drill guide 400 (and more particularly the conical-shaped alignment portion 420) abuts a significant and substantially surface area of the conically-shaped inner guide surface 204 of the selected drill guide passage 202s to provide secure and stable engagement between the fixed angle drill guide 400 and the guide block 200. Additionally, the tapering outer diameter $d_{to}$ of the conical alignment surface 421 substantially corresponds to the tapering inner diameter $d_{ti}$ of the conically-shaped inner guide surface 204 of the drill guide passages 202 to further facilitate secure and stable engagement between the fixed angle drill guide 400 and the guide block 200.

In this manner, the fixed angle drill guide 400 (and more specifically the guide barrel 402) is positioned and maintained at a predetermined/predefined/fixed angular orientation within the selected drill guide passage 202s. As should be appreciated, the predetermined/predefined/fixed angular orientation of the fixed angle drill guide 400 and the selected drill guide passage 202s may be determined by anatomic considerations and other requirements or guidelines that facilitate secure anchoring of the bone plate 100 to the underling bone via the bone anchors 190. As indicated above, in one specific embodiment, the cone angle α defined by the inner guide surface 204 of the drill guide passages 202 is approximately 30 degrees, and the cone angle θ defined by the conical alignment surface 421 alignment portion 420 is also approximately 30 degrees. However, as further indicated above, cone angles α, θ of 30 degrees are exemplary, and other cone angles α, θ are also contemplated.

Once the guide barrel 402 and the longitudinal axis $L_F$ of the drill guide 400 is positioned at the fixed angular orientation within the selected drill guide passage 202s, the drill 180 or another type of cutting instrument may be passed through the longitudinal passage 410 and through the aligned bone screw opening 102 in the bone plate 100 to form a bore/opening in the underlying bone along the fixed longitudinal axis $L_F$, and/or one of the bone anchors 190 may passed through the longitudinal passage 410 and through the aligned bone screw opening 102 to anchor the bone anchor in the underlying bone at an angular orientation or trajectory along the fixed longitudinal axis $L_F$. Once the bore/opening is formed in the underlying bone and/or the bone anchor is anchored within the underlying bone, the fixed angle drill guide 400 may be removed via disengagement of the distal-most end portion 424 from the bone screw openings 102 in the bone plate 100 and removal of the distal portion 408 of the drill guide 400 from the selected drill guide passage 202s. The fixed angle drill guide 400 may then be used in association with another of the drill guide passages 202 to form another bore/opening in the underlying bone at a fixed angle and/or to anchor another of the bone anchors 190 within the bone at a fixed angle. Alternatively, the variable angle drill guide 300 may be used in association with another of the drill guide passages 202 to form another bore/opening in the underlying bone at a variable angle and/or to anchor another of the bone anchors 190 within the bone at a variable angle, or the guide block 200 may be removed from the bone plate 100 via loosening or unlocking the fastener 290 to permit disengagement of the guide block 200 from the bone plate 100.

Figure 15:
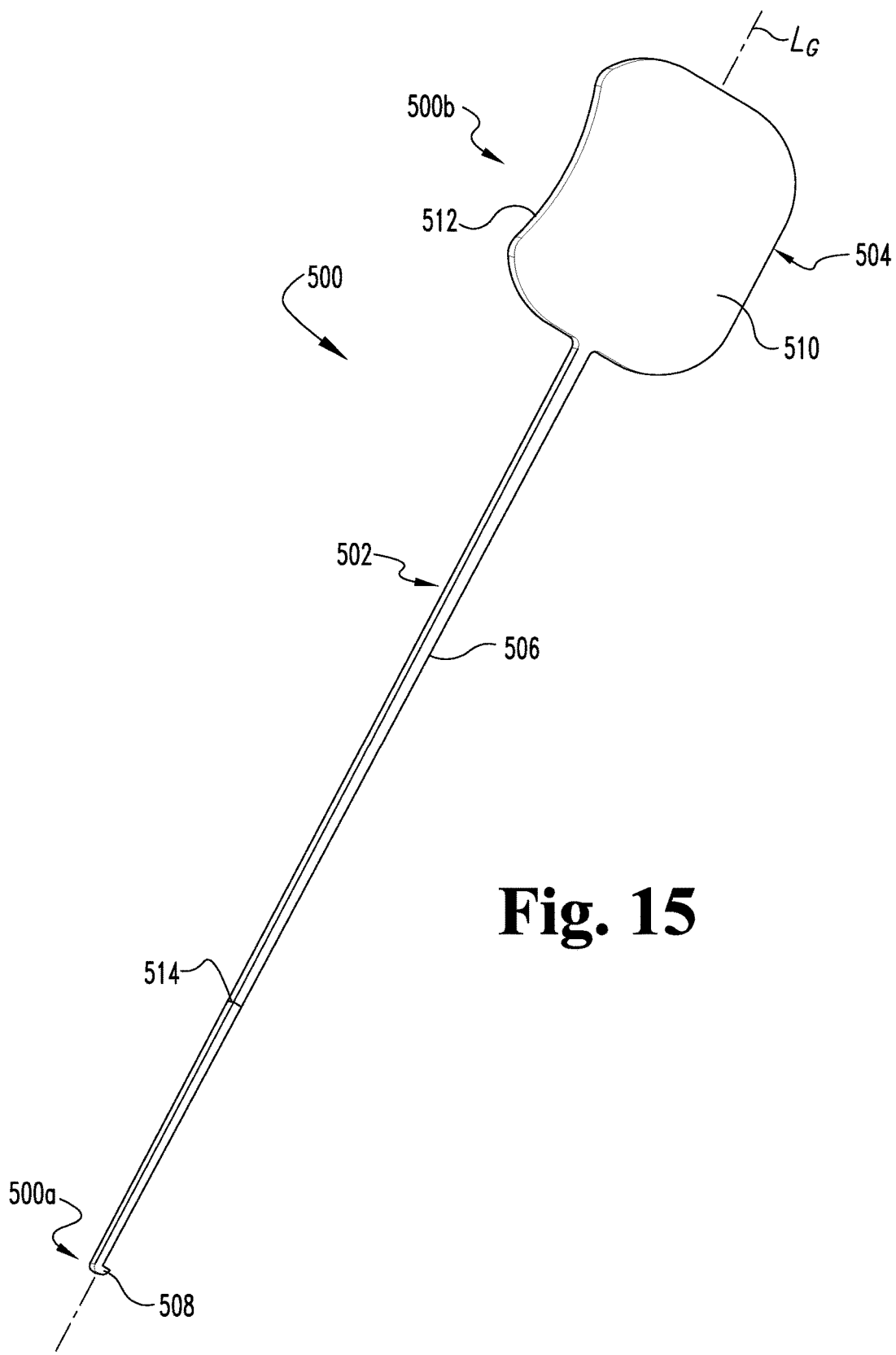
FIG. 15 is a perspective view of one embodiment of a depth gauge for use in association with the drill guide system of FIG. 1.

Referring to FIG. 15, the depth gauge 500 extends generally along a longitudinal gauge axis $L_G$ and includes a distal end 500a, a proximal end 500b, an elongate gauge portion 502, and a proximal handle or grasping portion 504. As will be discussed below, the depth gauge 500 is configured for use in association with both the variable angle drill guide 300 and the fixed angle drill guide 400 to measure the depth of a bore/opening formed in the underlying bone B and/or to provide an indication as to the appropriate length of the bone anchor 190 to be used in association with the bore/opening in the underlying bone B.

In the illustrated embodiment, the elongate gauge portion 502 is configured as an axial shaft or rod 506 having an enlarged distal end portion 508. In one embodiment, the axial shaft 506 has a generally rectangular cross section, and the enlarged distal end portion 508 has a hook-shaped configuration defining a laterally-extending shoulder and a convex or curved distal end surface. However, other shapes and configurations of the axial shaft 506 and the enlarged distal end portion 508 are also contemplated. Additionally, in the illustrated embodiment, the proximal handle portion 504 is configured as a generally flat/planar paddle or plate 510 defining a recessed or scalloped region 512 extending along a side edge of the paddle 510, each adapted to facilitate grasping and manipulation of the depth gauge 500. However, other shapes and configurations of the proximal handle portion 504 are also contemplated. Additionally, the axial shaft 506 includes a reference marking or indicia 514 positioned at a predetermined distance from the enlarged distal end portion 508, the purpose of which will be discussed below.

As illustrated in FIGS. 1 and 2, the elongate gauge portion 502 of the depth gauge 500 may be inserted through either the longitudinal passage 310 in the variable angle drill guide 300 or the longitudinal passage 410 in the fixed angle drill guide 400 to measure the depth of a bore/opening formed in the underlying bone B, which in turn may be used to select a bone screw 190 having an appropriate length for engagement within the bore/opening in the bone B. More specifically, the axial shaft 506 of the depth gauge 500 is insertable through the longitudinal passage 310 in the fixed angle drill guide 300 or the longitudinal passage 410 in the variable angle drill guide 400, and the hook-shaped distal end portion 508 may be hooked into engagement with the opposite side of the underlying bone B (i.e., the cortical bone surface adjacent the far end of the bore/opening extending through the bone B). The surgeon or other medical personnel then observes which of the scaled indicia 314, 414 along the longitudinal passage 310, 410 of the guide barrel 302, 402 is aligned with the reference marking 514 on the axial shaft 506 of the depth gauge 500, as viewed through the transverse opening/window 312, 412 in the guide barrel 302, 402. For example, if the reference marking 514 on the depth gauge 500 is aligned with the numeral "20" (indicia 314, 414) on the guide tube 302, 402, this provides an indication that a bone anchor 190 having a 20 mm length should be used in association with the measured bore/opening in the bone B.

In another embodiment, in instances where the bore/opening does not extend entirely through the bone B (i.e., a blind bore/opening), the distal end surface of the enlarged distal end portion 508 may be positioned in abutment against the bottom of the bore/opening, and the scaled indicia 314, 414 along the longitudinal passage 310, 410 of the guide barrel 302, 402 that is aligned with the reference marking 514 on the axial shaft 506 of the depth gauge 500 provides an indication as to the depth of the blind bore/opening in the bone B, and/or an indication as to the appropriate length of the bone anchor 190 to be used in association with the blind bore/opening. In a further embodiment, a reference marking or indicia (similar to that of the reference marking 514 of the depth gauge 500) may be positioned along the shaft 182 of the drill 180 at a predetermined distance from the distal end of the drill shaft 182. As should be appreciated, the drill shaft 182 of the drill 180 is insertable through the longitudinal passage 310 in the fixed angle drill guide 300 or the longitudinal passage 410 in the variable angle drill guide 400, and a bore/opening is formed in the underlying bone B. During the drilling operation, the surgeon or other medical personnel may observe which of the scaled indicia 314, 414 along the longitudinal passage 310, 410 of the guide barrel 302, 402 is aligned with the reference marking on the drill shaft 182, as viewed through the transverse opening/window 312, 412 in the guide barrel 302, 402. For example, if the reference marking on the drill shaft 182 is aligned with the numeral "10" (indicia 314, 414) on the guide barrel 302, 402, this provides an indication that the bore/opening has a depth of 10 mm, which can in turn be used to select a bone anchor 190 having an appropriate length corresponding to the depth of the bore/opening formed in the bone B.

Figure 16:
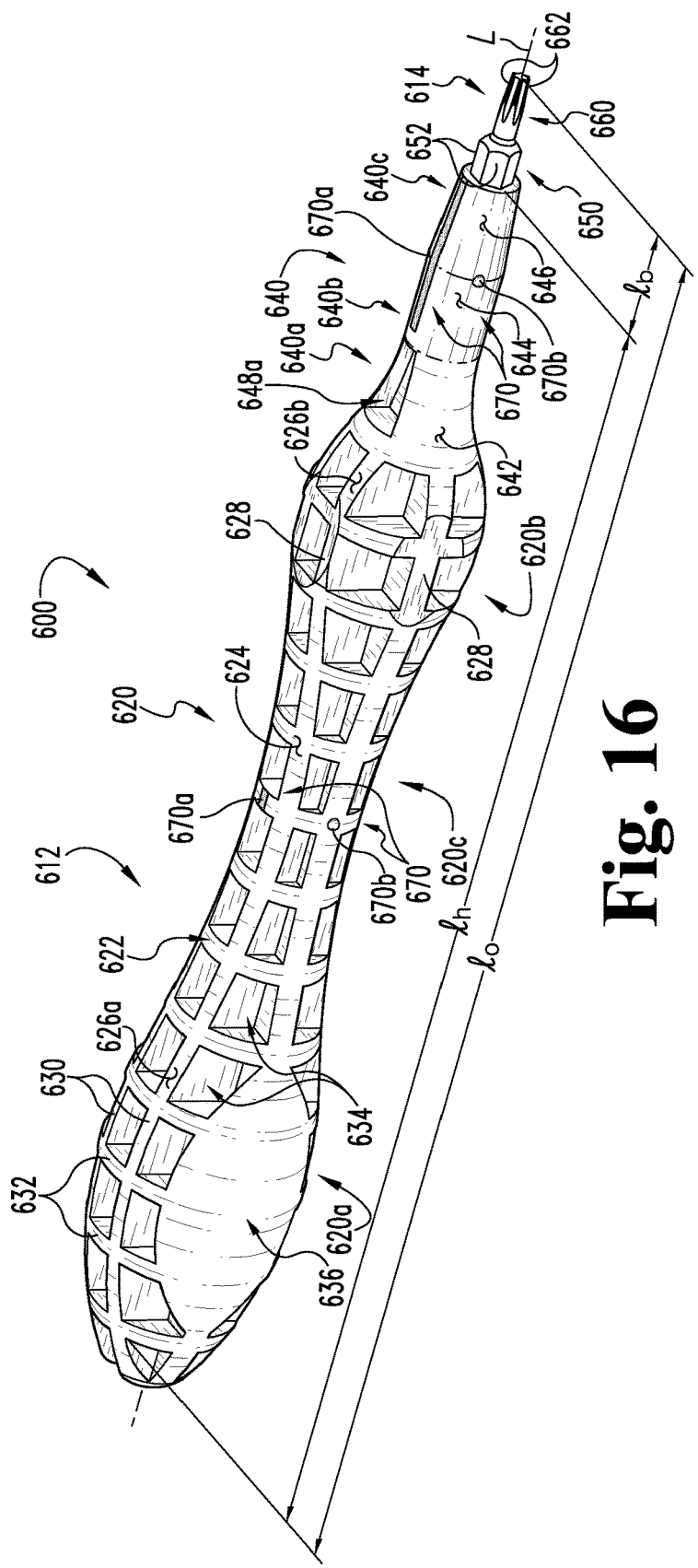
FIG. 16 is a perspective view of one embodiment of a driver instrument for use in association with the drill guide system of FIG. 1.

Referring to FIG. 16, illustrated therein is the orthopedic driver instrument 600 according to one form of the invention. The driver instrument 600 has an overall length extending along a longitudinal axis L, and generally includes a proximal handle 612 and a distal driver tip or bit 614. In one embodiment, the driver instrument 600 is configured for use in association with orthopedic surgical procedures to manipulate and drive bone screws or other types of bone anchors into bone. As will be discussed below, the driver instrument 600 includes a distal end portion that is releasably engagable with the head of a bone screw to manipulate the bone screw to an anchor location or surgical site for driving engagement into bone. However, it should be appreciated that the orthopedic driver instrument 600 may be used in association with a variety of orthopedic surgeries or procedures, and may be used to manipulate various types and configurations of bone anchors and/or other orthopedic devices including bone shaping/cutting devices.

The proximal handle 612 and the distal bit 614 of the driver instrument 600 are formed of biocompatible materials including, for example, plastic materials such as polyethylene or other polymeric materials, and metallic materials such as stainless steel or titanium. However, other suitable biocompatible materials are also contemplated including other types of plastic or polymeric materials, other types of metallic materials, and/or composite materials. In one specific embodiment, the proximal handle 612 is made of a plastic material, and the distal bit 614 is made of a metallic material. However, it should be appreciated that other combinations of materials are also contemplated. In one aspect of the invention, the proximal handle 612 is made of a plastic injection molded material, and is formed via a plastic injection molding process. In another aspect of the invention, the distal bit 614 is made of a metal injection molded material, and is formed via a metal injection molding process. However, it should be understood that other types of materials and formation processes or manufacturing techniques are also contemplated for use in association with the present invention.

In the illustrated embodiment, the proximal handle 612 includes a gripping portion or main body 620, and a stem portion or elongate shaft 640 extending axially from the gripping portion 620. Additionally, the distal bit 614 includes a shank or attachment portion 650, and a shaped end or engagement portion 660 configured for engagement with a bone anchor such as, for example, the head of a bone screw or other types of fastener devices. In one embodiment, the stem portion 640 of the proximal handle 612 is over molded about the shank portion 650 of the distal bit 614. In this manner, the proximal handle 612 and the distal bit 614 are integral with one another so as to define a unitary driver instrument 600 wherein the distal bit 614 is permanently attached/engaged to the proximal handle 612. However, other embodiments are also contemplated wherein the proximal handle 612 and the distal bit 614 are detachable/disengagable from one another.

In the illustrated embodiment of the proximal handle 612, the gripping portion 620 extends generally along the longitudinal axis L and includes a proximal region 620a, a distal region 620b, and a central region 620c extending between the proximal and distal regions 620a, 620b. The gripping portion 620 is sized, shaped and configured to provide an ergonomic design that is readily grasped and manipulated by a user (i.e., a surgeon). In one embodiment, the gripping portion 620 has an outer surface 622 defining a longitudinally-extending concave surface contour 624 extending along the central region 620c, and longitudinally-extending convex surface contours 626a, 626b extending along the proximal and distal regions 620a, 620b, respectively, and arranged on opposite sides of the longitudinally-extending concave surface contour 624. In another embodiment, the transitions between the proximal, distal and central regions 620a, 620b and 620c are smooth so as to avoid sharp corners or abrupt transitions between the regions of the handle gripping portion 620. In one embodiment, the proximal region 620a defines a maximum outer diameter $d_1$, the distal region 620b defines a maximum outer diameter $d_2$, and the central region 620c defines a minimum outer diameter $d_3$. In one embodiment, the minimum outer diameter $d_3$ of the central region 620c is less than both the maximum outer diameters $d_1$ and $d_2$ of the proximal and distal regions 620a, 620b. In another embodiment, the maximum outer diameter $d_1$ of the proximal region 620a is greater than the maximum outer diameter $d_2$ of the distal region 620b. However, other configurations of the gripping portion 620 are also contemplated, including embodiments where the maximum outer diameters $d_1$ and $d_2$ of the proximal and distal regions 620a, 620b are substantially equal to one another.

In some embodiments of the driver instrument 600, the outer surface 622 of the gripping portion 620 further defines a plurality of flats or flattened regions 628 dispersed along and/or about the distal longitudinally-extending convex surface contour 626b of the distal region 620b. In the illustrated embodiment, the outer surface 622 defines four flattened regions 628 dispersed uniformly about a circumference of the distal region 620b of the gripping portion 620. However, other embodiments are also contemplated wherein flattened regions may be located along other regions of the gripping portion 620 including, for example, the proximal longitudinally-extending convex surface contour 626a of the proximal region 620a. It should be appreciated that the size of the flattened regions 628 may vary, and that any number of the flattened regions 628 may be dispersed along and/or about various regions of the gripping portion 620, including embodiments of the driver instrument 600 that do not include any of the flattened regions 628.

Additionally, in the illustrated embodiment, the gripping portion 620 includes a plurality of longitudinally-extending ribs 630 and a plurality of transversely-extending ribs 632 extending between adjacent pairs of the longitudinally-extending ribs 630 so as to define a grid pattern. The longitudinally-extending ribs 630 cooperate with the transversely-extending ribs 632 to define a plurality of hollow recessed regions or indentations/depressions 634 dispersed along the length of the gripping portion 620 and about the circumferential periphery of the gripping portion 620, thereby providing the gripping portion 620 with a hollow grid pattern along its length and about its perimeter. As should be appreciated, the longitudinally-extending ribs 630, the transversely-extending ribs 632, and the recesses 634 cooperate to provide the gripping portion 620 with a frictional non-slip configuration to facilitate secure grasping and handling of the proximal handle 612 by the surgeon or other medical personnel. As should be further appreciated, the ribbed configuration of the proximal handle 612 defining the hollow grid pattern significantly reduces the amount of material required to form the proximal handle 612, and does so without a significant reduction in the strength and structural integrity of the proximal handle 612. The ribbed configuration and hollow grid pattern of the gripping portion 620 also reduce the overall weight of the driver instrument 600.

In the illustrated embodiment of the driver instrument 600, the gripping portion 620 of the proximal handle 612 may be provided with one or more non-ribbed regions 636 located along and about one or more regions of the gripping portion 620 including, for example, the proximal longitudinally-extending convex surface contour 626a. In the illustrated embodiment, the non-ribbed regions 636 define the same localized curvature as the adjacent ribbed regions of the gripping portion 620 which include the longitudinally-extending ribs 630 and the transversely-extending ribs 632, thereby providing the proximal handle 612 with a substantially continuous and uniform outer surface. As should be appreciated, the non-ribbed regions 636 provide the gripping portion 620 with a relatively smooth, uninterrupted gripping surface to promote comfortable handling and rotation of the driver instrument 600 by the surgeon, particularly when driving a large number of bone screws or fasteners into bone. Additionally, in the illustrated embodiment, the gripping portion 620 defines a pair of the non-ribbed regions 636 located on opposite sides of the proximal handle 612. However, it should be appreciated that the gripping portion 620 may be provided with any number of the non-ribbed regions 636, and that the non-ribbed regions 636 may be dispersed along and/or about various regions of the gripping portion 620.

In the illustrated embodiment of the proximal handle 612, the stem portion 640 extends from the gripping portion 620 generally along the longitudinal axis L, and the stem portion 640 and the gripping portion 620 together form a monolithic, single-piece handle structure. The stem portion 640 generally includes a proximal transition region 640a extending axially from the distal end of the gripping portion 620, a central region 640b extending axially from the proximal transition region 640a, and a distal region or end portion 640c extending axially from the central region 640b. However, it should be appreciated that other shapes and configurations of the stem portion 640 are also contemplated.

In one embodiment, the proximal transition region 640a is conically-shaped and has an outer concave surface 642 extending along the longitudinal axis L and defining an inward taper in a proximal-distal direction. In another embodiment, the central region 640b is cylindrically-shaped and has an outer cylindrical surface 644 defining a maximum outer diameter $d_4$. In a further embodiment, the distal region or end portion 640c is conically-shaped and has an outer conical surface 646 extending along the longitudinal axis L and also defining an inward taper in a proximal-distal direction. However, other shapes, sizes and configurations of the proximal transition region 640a, the central region 640b, and the distal region 640c are also contemplated.

In one specific embodiment, the maximum outer diameter $d_4$ of the central region 640b is less than both the maximum outer diameters $d_1$ and $d_2$ of the proximal and distal regions 620a, 620b of the gripping portion 620. In another specific embodiment, the maximum outer diameter $d_4$ of the central region 640c is less than or substantially equal to the minimum outer diameter $d_3$ of the central region 620c of the gripping portion 620. However, it should be appreciated that other embodiments are also contemplated where the relative size of the central region 640b of the stem portion 640 varies relative to the regions of the gripping portion 620.

Additionally, the stem portion 640 may include a pair of recesses or indentations 648a, 648b extending along the length of the proximal transition portion 642 and positioned on opposite sides of the stem portion 640. However, other embodiments are also contemplated where any number of the recesses or indentations may be provided along/about any region of the stem portion 640, including embodiments that do not include any recesses or indentations along/about the stem portion 640.

In the illustrated embodiment, the distal bit 614 includes a proximal shank portion 650 and a distal engagement portion 660. In one embodiment, the proximal shank portion 650 has a non-circular shape so as to facilitate secure engagement of the distal bit 614 with the proximal handle 612 and to inhibit rotational movement of the distal bit 614 relative to the proximal handle 612. In one specific embodiment, the proximal shank portion 650 is provided with one or more flats or flattened regions 652. In another specific embodiment, the proximal shank portion 650 is hexagonally-shaped. However, other shapes and configurations of the proximal shank portion 650 are also contemplated including, for example, a star shape, a Torx shape, a square shape, a triangular shape, or other shapes suitable to inhibit rotational movement of the distal bit 614 relative to the proximal handle 612.

In the illustrated embodiment, the distal engagement portion 660 has a non-circular shape configured to facilitate rotational driving engagement of the distal bit 614 with the head of a bone screw or another type of bone anchor or orthopedic device. In one specific embodiment, the distal engagement portion 660 includes a plurality of radially-extending splines 662 extending along a length of the distal engagement portion 660. In another specific embodiment, the distal engagement portion 660 is star-shaped and is sized and shaped for receipt within a correspondingly sized/shaped driver opening in the head of the bone screw to facilitate rotational engagement of the distal bit 614 with the head of the bone screw. However, other shapes and configurations of the distal engagement portion 660 are also contemplated including, for example, a Phillips shape, a Torx shape, a hexagonal shape, a cruciform shape, a square shape, a triangular shape, a flat blade shape, or other shapes suitable to provide driving rotational engagement of the distal bit 614 with the head of the bone screw. Additionally, in some embodiments, the distal engagement portion 660 defines an inward taper in a proximal-distal direction to facilitate insertion of the distal engagement portion 660 into the driver opening in the head of the bone screw, and to provisionally and releasably engage and capture/retain the bone screw on the distal bit 614 to facilitate removal from packaging, handling between the nurse (or other medical personnel) and the surgeon, and positioning and manipulation of the bone screw to the targeted anchor location or surgical site. As should be appreciated, provisionally and releasably engaging the distal engagement portion 660 with the bone screw tends to reduce the length, complexity and overall cost of the surgical procedure.

In the illustrated embodiment of the driver instrument 600, the proximal handle 612 has an overall handle length $l_h$ and the distal bit 614 has a bit length $l_b$ extending from the proximal handle 612 that cooperate with one another to provide the driver instrument 600 with an overall instrument length $l_o$. As should be appreciated, the distal bit 614 includes a proximal portion that is over molded by and encapsulated within the stem portion 640 of the proximal handle 612. In one embodiment, the overall handle length $l_h$ is at least twice the bit length $l_b$. In another embodiment, the overall handle length $l_h$ is at least three times the bit length $l_b$. In a further embodiment, the overall handle length $l_h$ is at least four times the bit length $l_b$.

As indicated above, in one aspect of the invention, the proximal handle 612 is made of a plastic injection molded material and is formed via a plastic injection molding process, and in another aspect of the invention, the distal bit 614 is made of a metal injection molded material and is formed via a metal injection molding process. However, it should be understood that other types of materials and formation processes or manufacturing techniques are also contemplated. In one embodiment, the distal bit 614 is initially formed via the metal injection molding process, followed by formation of the proximal handle 612 via the plastic injection molding process wherein the stem portion 640 of the proximal handle 620 is over molded about the proximal shank portion 650 of the distal bit 614. In this manner, the proximal handle 612 and the distal bit 614 are integral with one another so as to define a unitary driver instrument 600 wherein the distal bit 614 is permanently attached/engaged to the proximal handle 612. Additionally, it should be appreciated that forming the distal bit 614 via a metal injection molding process eliminates machining steps or processes commonly associated with the fabrication/manufacturing of conventional driver instruments. In some embodiments, the distal bit 614 is heat treated or hardened subsequent to the metal injection molding process to provide additional strength to the distal bit. However, the distal bit 614 does not require any significant machining steps or processes subsequent to the metal injection molding process. As should be appreciated, elimination of machining steps/processes eliminates significant manufacturing costs and provides substantial savings in the production of the distal bit 614.

In a further aspect of the invention, the orthopedic driver instrument 600 is contemplated for use in association with a single surgery or orthopedic procedure, followed by permanent disposal of the driver instrument 600. As should be appreciated, disposal of the driver instrument 600 after a single surgery or orthopedic procedure eliminates the need to clean and sterilize the driver instrument 600, which in turn reduces the overall cost associated with use of the driver instrument 600. Additionally, it should be further appreciated that the cost of producing the orthopedic driver instrument 600 is approximately one-seventh (or less than 15%) of the cost of producing a conventional/traditional orthopedic driver instrument 600. These cost reductions are the result of a significant reduction in material costs, as well as a substantial reduction in the formation/fabrication cost of producing the orthopedic driver instrument 600. Significant reductions in the cost of producing the orthopedic driver instrument 600 are realized by forming the distal bit 614 via the metal injection molding process and forming the proximal handle 612 via the plastic injection molded process, including over molding of the stem portion 640 of the proximal handle 620 about the proximal shank portion 650 of the distal bit 614.

As indicated above, the ribbed configuration of the proximal handle 612 provides the gripping portion 620 with an ergonomic non-slip configuration, and also results in a significant reduction in the amount of material required to form the proximal handle 612 without a significant reduction in the strength and structural integrity (i.e., performance) of the proximal handle 612. Additionally, the distal bit 614 satisfies high tolerance level requirements via the metal injection molding process, which further provides repeatability from part to part, thereby eliminating the manufacturing/fabrication costs normally associated with performing significant machining processes on the components of the driver instrument. Since formation of parts via a metal injection molding processes is limited to parts having a relatively short length, the overall length of the distal bit 614 is sized to be significantly less than the overall length of the proximal handle 612. As indicated above, in some embodiments, the overall handle length $l_h$ is at least twice the bit length $l_b$. In other embodiments, the overall handle length $l_h$ is at least three or four times the bit length $l_b$. The relatively shorter length of the distal bit 614 is accommodated by providing the plastic proximal handle 612 with an elongate shaft or stem portion 640 formed integral with the main body 620 of the proximal handle 612 via the plastic injection molding process, and with the elongate stem portion 640 over molded about the proximal end portion of the distal bit 614 to form an integral driver instrument. As should be appreciated, conventional/traditional driver instruments typically include metallic drive shafts that have a significantly greater length compared to the much shorter length of the driver bit 614, thereby precluding formation of the metallic drive shaft of conventional/traditional driver instruments by way of a metal injection molding process.

In some embodiments, the orthopedic driver instrument 600 may be provided as a stand-alone instrument. However, in other embodiments, the orthopedic driver instrument 600 may be provided in a kit including an orthopedic support element such as, for example, a bone plate, along with a plurality of bone anchors such as, for example, bone screws.

In some embodiments, the orthopedic driver instrument 600 may include indexing markings or indicia 670 positioned along one or more regions of the proximal handle 612 and/or the distal driver bit 614. As will be discussed in detail below, the indexing markings or indicia 670 provide the surgeon or other medical personnel with a visual or tactile indication as to rotational displacement of the driver instrument 600 to manually control or limit the driving torque applied to the bone screw or fastener being driven into bone tissue by the driver instrument 600. As should be appreciated, controlling or limiting the amount of torque applied to the bone screw or fastener minimizes risks associated with overtightening and/or undertightening of the bone screw including, for example, stripping of the internal threads in the bone tissue, damage to associated implants or other structures to which the bone screw is attached, and/or loosening or back out of the bone screw from the bone tissue.

In the illustrated embodiment of the driver instrument 600, the indexing markings 670 are positioned along the central and distal regions 640b, 640c of the stem portion 640. However, it should be appreciated that the indexing markings 670 may be positioned along other regions/portions and at other locations of the proximal handle 612 and/or the distal driver bit 614. For example, indexing markings 670 may be positioned along the proximal transition region 640a of the stem portion 640, and/or along any region of the gripping portion 620 of the proximal handle 612 including, for example, along the ribs 630, 632 and/or the non-ribbed region 636 of the gripping portion 620. In the illustrated embodiment, the indexing markings or indicia 670 positioned along the central region 620c of the gripping portion 620, although providing indexing markings 670 along the proximal region 620a and/or the distal region 620c of the gripping portion 620 is also contemplated. Additionally, in still other embodiments, indexing markings 670 may be positioned along the proximal shank portion 650 and/or the distal engagement portion 660 of the distal driver bit 614.

In the illustrated embodiment of the driver instrument 600, the indexing markings 670 are provided as lines or stripes 670a and raised bumps or protrusions 670b. In the illustrated embodiment, the lines/stripes 670a are provided as thick, black, solid and continuous linear markings. However, in other embodiments, the lines/stripes 670a may have other thickness (i.e., thin/narrow lines), may be provided in other colors (i.e., red, white, etc.), may be provided with a divided configuration (i.e., a double line), may be provided with a discontinuous configuration (i.e., a dashed or broken line), may be provided with a non-linear configuration (i.e., a curved or curvilinear line, circular shapes or dots), or may have any other suitable configuration to provide a visually perceptible indication as to the rotational position and/or rotational displacement of the driver instrument 600. Additionally, in the illustrated embodiment, the raised bumps or protrusions 670b are provided as hemispherical-shaped circular protrusions. However, in other embodiments, the raised bumps or protrusions 670b may have other shapes and configurations (i.e., star, square, rectangular, triangular, polygonal, elliptical, ovular, etc.), may be colorless or may be provided in a variety of different colors, or may have any other suitable configuration to provide a tactilely (and possibly visually) perceptible indication as to the rotational position and/or rotational displacement of the driver instrument 600.

It should be appreciated that other types of indexing markings or indicia are also contemplated for use in association with the driver instrument 600 including, for example, dots or circular shapes, arrows, non-linear shapes, symbols, letters, numbers, colors, or any other visually or tactilely perceptible marking or indicia. Additionally, it should be appreciated that the indexing marking or indicia 670 may be provided as laser markings or etchings, printed markings, painted markings, silk screened markings, inscriptions, engravings, grooves, recesses, depressions, impressions, raised features, colorations, discolorations, or any other suitable marking or indicia to provide a visually or tactilely perceptible indication as to the rotational position and/or rotational displacement of the driver instrument 600.

In the illustrated embodiment, each set, pair or group 670a, 670b of the indexing markings or indicia 670 includes at least two markings/indicia that are angularly offset from one another relative to the longitudinal axis L about a circumference of the driver instrument 600. In one embodiment, the indexing markings 670a, 670b are each provided in pairs of indexing markings positioned on opposite sides of the driver instrument 600. It is noted that only one of the indexing markings 670a, 670b of each pair is illustrated in FIG. 16, it being understood that another marking/indicia is positioned on the opposite side of the driver instrument 600. In other words, the pairs of indexing markings 670a, 670b are offset from one another by about 180 degrees and are positioned on opposite sides of the driver instrument 600. However, it should be understood that in other embodiments, each set/pair/group of the indexing markings 670a, 670b may include any number of markings/indicia including a single marking, three markings, or four or more markings positioned about a circumference of the driver instrument 600, and preferably angularly offset from one another in a substantially uniform manner (i.e., three indexing markings angularly offset by 120°, four indexing markings angularly offset by 90°, etc.). It should also be understood that the indexing markings or indicia 670 of a set/pair/group need not necessarily be positioned at the same axial location along the longitudinal axis L, but may instead by axially offset from one another along the longitudinal axis L.

In some embodiments, each of the indexing markings 670 of a set/pair/group may be of the same type/configuration (i.e., the indexing markings of a set/pair/group are configured identical to one another). However, in other embodiments, the indexing markings 670 of a set/pair/group may have different types/configurations or may be provided with different distinguishing features or characteristics to facilitate visual or tactile recognition of the particular rotational position or rotational displacement of the driver instrument 600 during driving of a screw or fastener into bone tissue. For example, in one embodiment, the indexing markings 670a may include a solid line on one side of the driver instrument (as shown in FIG. 16) and a divided/double line on the opposite side of the driver instrument to provide a degree of differentiation if desired to indicate different rotational positions or displacement of the driver instrument 600. In other embodiments, the indexing markings 670a may include a thick line on one side of the driver instrument (as shown in FIG. 16) and a thinner line on the opposite side of the driver instrument, a continuous line on one side of the driver instrument (as shown in FIG. 16) and a dashed or broken line on the opposite side of the driver instrument, a black line on one side of the driver instrument (as shown in FIG. 16) and a line of a different color on the opposite side of the driver instrument. Similarly, the indexing markings/indicia 670b may include a circular bump/protrusion on one side of the driver instrument (as shown in FIG. 16) and a bump/protrusion having a different shape/configuration on the opposite side of the driver instrument to provide a degree of differentiation if desired to indicate different rotational positions or displacement of the driver instrument 600. In other embodiments, the indexing markings 670b may include a bump/protrusion of a first color on one side of the driver instrument and a bump/protrusion of a different color on the opposite side of the driver instrument.

In still other embodiment, one of the indexing markings/indicia 670 of a set/pair/group may be of a first type or have a first feature/characteristic, and at least one other of the indexing markings/indicia 670 may be of a second type or have a second feature/characteristic that is visually or tactilely distinguishable from the first type. The distinguishing type/feature/characteristic may be different colors, shapes, symbols, letters, numbers, or any other visually distinguishable type, feature or characteristic. In one embodiment, at least one of the indexing markings/indicia 670 may be provided with a first color (i.e., red), and at least one of the indexing markings/indicia 670 may be provided with a different second color (i.e., black or blue). In one exemplary embodiment, two of the indexing markings/indicia positioned generally diametrically opposite one another may be provided with a first color (i.e., red), and two of the indexing markings/indicia positioned generally diametrically opposite one another may be provided with a different second color (i.e., black or blue). In another embodiment, at least one of the indexing markings/indicia may have a first shape (i.e., a dot) and at least one other of the indexing markings/indicia 670 may have a different second shape (i.e., a dash/line). Additionally, in another exemplary embodiment, the indexing markings/indicia 670 of a set/pair/group may have alternating or staggered types/features/characteristics such that every other indexing marking/indicia 670 has an alternating type/feature/characteristic (i.e., red-blue-red-blue or dot-dash-dot-dash, etc.). In still another exemplary embodiment, the indexing markings/indicia 670 of a set/pair/group may have sequential features/characteristics to indicate sequential rotational positions or displacement of the driver instrument 600 (i.e., 1-2-3-4 or A-B-C-D, etc.). As indicated above, providing the indexing markings or indicia 670 with distinguishing features or characteristics may promote visual or tactile recognition of the degree of angular displacement of the driver instrument 600 during driving of a screw or fastener into bone tissue.

As indicated above, the indexing markings or indicia 670 provide the surgeon or other medical personnel with a visual and/or tactile indication as to rotational position or rotational displacement of the driver instrument 600 to manually control or limit the driving torque applied to the bone screw or fastener being driven into bone tissue by the driver instrument 600. In one embodiment, as the bone screw or fastener is being driven into bone tissue by the driver instrument 600, at a point prior to the bone screw being fully driven or engaged in the bone tissue, the surgeon is provided with a provisional indication or feedback that the bone screw is approaching or near its fully engaged or locked state. In one embodiment, the provisional indication or feedback may be provided when a lower surface of the screw head (or another portion of the screw) engages or abuts a corresponding surface on a bone plate or another type of orthopedic implant. In one exemplary embodiment, the surgeon may be provided with a "tactile feel" associated with engagement of the screw head (or another portion of the screw) with another feature associated with an implant or device. However, in other embodiments, the provisional indication or feedback may be provided via a visual or audible indication (i.e., via a visual alignment of one structural feature relative to another structural feature, or via a sound generated by engagement of one structural feature with another structural feature).

Once the provisional indication/feedback is received or perceived by the surgeon, the driver instrument 600 (and the bone screw) is rotated or indexed an additional predetermined amount/degree to the fully engaged or locked state of the bone screw or fastener. As should be appreciated, the additional predetermined amount/degree of rotational or angular displacement may be measured by the indexing markings or indicia 670, 670a, 670b. For example, in one embodiment, the additional predetermined amount/degree of rotational or angular displacement may be one-half turn or 180° of additional rotational displacement, as measured by the angular passage of a certain number of the indexing markings or indicia 670, 670a, 670b from a selected reference position or location. In other embodiments, the additional predetermined amount/degree of rotational or angular displacement may be one-quarter turn or 90° of additional rotational displacement, three-quarter turn or 270° of additional rotational displacement, or full turn or 360° of additional rotational displacement, as measured by the angular passage of a certain number of the indexing markings or indicia 670, 670a, 670b from a selected reference position or location. However, it should be understood that the additional predetermined amount/degree of rotational or angular displacement may vary and is not limited to the exemplary embodiments set forth above.

In the illustrated embodiment of the driver instrument 600, the visually-perceptible indexing markings or indicia 670a include two indexing markings/indicia positioned on opposite sides of the driver instrument 600. Once the provisional indication/feedback is received or perceived by the surgeon, the driver instrument 600 (and the bone screw) may be rotated or indexed an additional one-half turn or 180° to the fully engaged or locked state of the bone screw or fastener, as measured by rotation of the driver instrument 600 until the marking/indicia 670a on the opposite side of the driver instrument is positioned at or near the original angular position of the other marking/indicia 670a. However, as indicated above, the driver instrument 600 may be provided with three or more of the indexing markings/indicia 670a to provide additional resolution or gradations to accommodate other degrees of rotational displacement or indexing from the initial rotational position to the fully engaged or locked rotational position of the bone screw or fastener.

Additionally, in the illustrated embodiment of the driver instrument 600, the tactilely-perceptible indexing markings or indicia 670b include two indexing markings/indicia positioned on opposite sides of the driver instrument 600. Once the provisional indication/feedback is received or perceived by the surgeon, the driver instrument 600 (and the bone screw) may be rotated or indexed an additional one-half turn or 180° to the fully engaged or locked state of the bone screw or fastener, as measured by rotation of the driver instrument 600 until the marking/indicia 670b on the opposite side of the driver instrument is positioned at or near the original angular position of the other marking/indicia 670b. However, as indicated above, the driver instrument 600 may be provided with three or more of the indexing markings/indicia 670b to provide additional resolution or gradations to accommodate other degrees of rotational displacement or indexing from the initial rotational position to the fully engaged or locked rotational position of the bone screw or fastener. With regard to the tactilely-perceptible indexing markings or indicia 670b, the surgeon may use one hand (i.e., the right hand) to grasp the gripping portion 620 of the proximal handle 614 to rotate the driver instrument 600 and drive the screw/fastener, and may use one or more fingers of the other hand (i.e., the left hand) to provide a tactile feel of the indexing markings/indicia 670b to determine the rotational position or displacement of the driver instrument 600 between the initial rotational position to the fully engaged or locked rotational position of the bone screw or fastener.

As should be appreciated, the indexing markings/indicia 670, 670a, 670b associated with the orthopedic driver instrument 600 provide the surgeon with a visual or tactile indication as to the appropriate amount of additional rotational or angular displacement of the driver instrument 600 from an initial rotational position (i.e., the rotational position at which a provisional indication/feedback is received or perceived by the surgeon) to a final rotational position corresponding to the fully engaged or locked state of the bone screw or fastener, thereby minimizing the negative effects and potential risks associated with overtorquing, overtightening and/or undertightening the bone screw or fastener.

Further details regarding the orthopedic driver instrument 600 are described in commonly-owned International PCT Application No. 2014/072155, the contents of which are incorporated herein by reference in their entirety.

In another aspect of the invention, the components of the drill guide system 20 may be provided in a surgical kit including the bone plate 100, the guide block 200, the fixed angle drill guide 300, and the variable angle drill guide 400. In some embodiments, the surgical kit may further include the depth gauge 500. In other embodiments of the kit, the guide block 200 may be pre-assembled with the bone plate 100 via the fastener 290 to provide a pre-assembled plate/guide block assembly, as illustrated in FIG. 6. In another embodiment, the surgical kit may further include the drill 180 or other types of cutting instruments. In still other embodiments, the surgical kit may include a plurality of the bone screws 190 or other types of bone anchors, and may further include the driver instrument 600 to drive the bone screws 190 or other types of bone anchors, screws or fasteners into engagement with bone. It should be appreciated that the components of the surgical kit may be provided together in a single container or other types of packaging suitable for use in association with surgical kits.

As should now be appreciated, both the variable angle drill guide 300 and the fixed angle drill guide 400 included in the drill guide system 20 are structured and configured to cooperate with any of the drill guide passage 202 in the guide block 200 and the aligned bone screw opening 102 in the bone plate 100 to form a bore/channel in the underlying bone at either a predetermined/predefined angular orientation or a variable angular orientation relative to the bone plate 100 via the drill 180 or another type of cutting instrument 180, and/or to anchor a bone anchor 190 in the underlying bone at either a predetermined/predefined angular orientation or a variable angular orientation relative to the bone plate 100. Additionally, the variable angle drill guide 300 is also structured and configured to cooperate with the central passage 240 in the guide block 200 and the aligned fastener opening 140 in the bone plate 100 to form a bore/channel in the underlying bone at a variable angular orientation relative to the bone plate 100 via the drill 180 or another type of cutting instrument 180, and/or to anchor a bone anchor 190 in the underlying bone at a variable angular orientation relative to the bone plate 100.

As should also be appreciated, prior drill guide systems are capable of forming bores in the underlying bone at either predetermined/predefined angular orientations or variable angular orientations, but not both. For example, some prior drill guide systems provide drill guides that are pre-assembled to a bone plate to form bores/openings in the underlying bone at fixed angle trajectories, but do not allow for the formation of bores/openings at variable angle trajectories. Additionally, some prior drill guide systems utilize a guide block that is specifically designed and configured for use in association with a fixed angle drill guide to form bores/openings in the underlying bone at fixed angle trajectories, while other prior drill guide systems utilize a guide block that is specifically designed configured for use in association with a variable angle drill guide to form bores/openings in the underlying bone at variable angle trajectories. However, prior drill guide systems are not configured such that passages in the guide block engage and cooperate with both a fixed angle drill guide and a variable angle drill guide to form bores/openings in the underlying bone at either fixed or variable angle trajectories. Additionally, the use of prior drill guide systems to form bores/openings in the underlying bone at both fixed and variable angle trajectories can only be achieved by removing the guide block from the bone plate. As a result, the surgeon is not able to quickly and efficiently interchange between fixed angle and variable angle drilling methods.

While the disclosed drill guide system and method for placement of bone screws using both variable angle and fixed angle placement methods have been described for use in association with a bone plate to treat fractures or injuries of the distal radius bone, it should be understood that the disclosed system and method may also be used in association with other surgical procedures and/or in the treatment of other bones or bony structures. In reading the claims, words such as "a", "an", "at least one", and "at least a portion" are not intended to limit the claims to only one item unless specifically stated to the contrary. Additionally, when the language "at least a portion" and/or "a portion" is used, the claims may include a portion and/or the entire item unless specifically stated to the contrary. Furthermore, when the term "distal" is used with respect to a structure, the term refers to the far end of the structure, and when the term "proximal" is used with respect to a structure, the term refers to the near end of the structure.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A drill guide system, comprising:
   a bone plate including a plurality of bone screw openings sized to receive bone screws;
   a guide block including at least two drill guide passages extending therethrough, the guide block selectively and removably engaged with the bone plate wherein the drill guide passages are substantially aligned with corresponding ones of the bone screw openings in the bone plate, each of the drill guide passages having a conically-shaped inner guide surface;
   a fixed angle drill guide including a distal portion selectively positioned within a selected one of the drill guide passages in the guide block and having a conically-shaped outer guide surface matingly engaged with the conically-shaped inner guide surface of a selected drill guide passage to maintain orientation of the fixed angle drill guide at a predetermined fixed angular orientation relative to the guide block and the bone plate; and
   a variable angle drill guide including a distal portion selectively positioned within a selected one of the drill guide passages in the guide block and having an outer guide surface sized smaller than the conically-shaped inner guide surface of a selected drill guide passage to permit orientation of the variable angle drill guide at a variable angular orientation relative to the guide block and the bone plate.

2. The drill guide system of claim 1 wherein the distal portion of the variable angle drill guide includes a distal end engaged within one of the bone screw openings in the bone plate that is substantially aligned with the selected one of the drill guide passage in which the variable angle drill guide is selectively positioned.

3. The drill guide system of claim 1 wherein the distal portion of the fixed angle drill guide includes a distal end engaged within one of the bone screw openings in the bone plate that is substantially aligned with the selected one of the drill guide passage in which the fixed angle drill guide is selectively positioned.

4. The drill guide system of claim 1 wherein the distal portion of the fixed angle drill guide and the distal portion of the variable angle drill guide each include a distal end having a non-circular configuration sized and shaped for mating engagement within a selected one of the bone screw openings in the bone plate having a corresponding non-circular configuration.

5. The drill guide system of claim 4 wherein the non-circular configuration of the distal ends of the drill guides are sized and shaped to provide snap-fit engagement within the selected one of the bone screw opening in the bone plate to provide tactile feedback indicative of the mating engagement between the distal end of the drill guide and the selected one of the bone screw openings.

6. The drill guide system of claim 4 wherein the non-circular configuration comprises a star-shaped configuration.

7. The drill guide system of claim 1 wherein the conically-shaped inner guide surface of the drill guide passages defines approximately a 30 degree cone; and
   wherein the variable angular orientation of the variable angle drill guide includes any angular orientation within the 30 degree cone.

8. The drill guide system of claim 1 wherein the fixed angle drill guide has a first bore extending therethrough and defining a first inner diameter; and
   wherein the variable angle drill guide has a second bore extending therethrough and defining a second inner diameter equal to the first inner diameter.

9. The drill guide system of claim 1 wherein a first of the drill guide passages in the guide block is arranged along a first axis; and
   wherein a second of the drill guide passages in the guide block is arranged along a second axis that is not parallel with the first axis.

10. The drill guide system of claim 1 wherein the guide block has a first surface facing an upper surface of the bone plate when the guide block is selectively engaged with the bone plate;
    wherein the guide block includes a second surface opposite the first surface; and
    wherein the conically-shaped inner guide surface of the drill guide passages extends from the second surface toward the first surface.

11. The drill guide system of claim 10 wherein each of the drill guide passages has a cylindrical-shaped inner surface extending from the conically-shaped inner guide surface to the first surface of the guide block.

12. The drill guide system of claim 10 wherein the conically-shaped inner guide surface of an adjacent pair of the drill guide passages intersect and overlap one another.

13. The drill guide system of claim 1 further comprising a locking element engaged with the guide block and the bone plate to selectively and removably engage the guide block to the bone plate.

14. The drill guide system of claim 13 wherein the locking element comprises a threaded fastener having a head portion abutting the guide block and a threaded portion engaged with the bone plate.

15. The drill guide system of claim 13 further comprising an alignment element extending between the guide block and the bone plate to maintain alignment of the guide block with the bone plate.

16. The drill guide system of claim 15 wherein the alignment element comprises a projection positioned within a recess.

17. The drill guide system of claim 1 wherein the guide block includes at least three of the drill guide passages.

18. The drill guide system of claim 1 wherein the bone plate includes a plate body having an elongate shaft portion and a triangular-shaped head portion extending from the elongate shaft portion;
    wherein the guide block has an outer periphery defining a shape substantially complementary to the triangular-shaped head portion of the plate body.

19. The drill guide system of claim 1 further comprising a plurality of bone screws each including a head portion and a threaded shank portion extending from the head portion and adapted for anchoring within bone; and
    wherein the bone screw openings in the bone plate each have an inner surface and a plurality of flexible fins integrally connected to and protruding radial inward from the inner surface, wherein the plurality of flexible fins are deflectable by the head portion of one of the bone screws inserted into a corresponding one of the bone screw openings to retain the bone screw therein.

20. The drill guide system of claim 1 further comprising a depth gauge including an elongate shaft having an indicia marking, the elongate shaft insertable through either of the fixed angle drill guide and the variable angle drill guide and into engagement with a bone surface associated with a bore formed in the bone; and
wherein the indicia marking on the elongate shaft of the depth gauge is generally aligned with an indicia marking on either the fixed angle drill guide or the variable angle drill guide feature to indicate an appropriate length of a bone anchor configured for anchoring within the bore in the bone.

21. The drill guide system of claim 1 further comprising an orthopedic driver instrument including:
a proximal handle;
a distal driver bit; and
a plurality of indexing markings or indicia positioned on an outer surface of the proximal handle and/or the distal driver bit to provide a visual or tactile indication as to a rotational position or rotational displacement of the orthopedic driver instrument to manually control or limit driving torque applied to a bone screw or fastener driven by the orthopedic driver instrument.

22. The orthopedic driver instrument of claim 21, wherein the plurality of indexing markings or indicia comprise visual markings positioned at different angular positions about the outer surface to provide a visual indication as to the rotational position or rotational displacement of the orthopedic driver instrument.

23. The orthopedic driver instrument of claim 22, wherein the visual markings comprise at least one of a line, dash, dot, shape, color, number, letter or symbol.

24. The orthopedic driver instrument of claim 21, wherein the plurality of indexing markings or indicia comprise tactile indicia positioned at different angular positions about the outer surface to provide a tactile indication as to the rotational position or rotational displacement of the orthopedic driver instrument.

25. The orthopedic driver instrument of claim 24, wherein the tactile indicia comprise at least one of a raised bump, projection, protrusion, recess, depression, impression, indentation or groove.

26. A surgical kit including the bone plate, the guide block, the fixed angle drill guide, and the variable angle drill guide of the drill guide system of claim 1.

27. The surgical kit of claim 26 wherein the guide block is engaged with the bone plate to provide a pre-assembled guide block and bone plate assembly.

28. The surgical kit of claim 26 further comprising at least one drill sized for passage through the fixed angle drill guide and the variable angle drill guide, the drill configured to form bores in the bone that are aligned with corresponding ones of the bone screw openings in the bone plate; and
a plurality of bone screws sized and configured for insertion through corresponding ones of the plurality of bone screw openings in the bone plate and into the bores formed in the bone to attach the bone plate to the bone; and
an orthopedic driver instrument including a proximal handle, a distal driver bit, and a plurality of indexing markings or indicia positioned on an outer surface of the proximal handle and/or the distal driver bit to provide a visual or tactile indication as to a rotational position or rotational displacement of the orthopedic driver instrument to manually control or limit driving torque applied to a bone screw or fastener driven by the orthopedic driver instrument.

29. The surgical kit of claim 26 further comprising a depth gauge including an elongate shaft having an indicia marking, the elongate shaft insertable through either of the fixed angle drill guide and the variable angle drill guide and into engagement with a bone surface associated with a bore formed in the bone; and
wherein the indicia marking on the elongate shaft of the depth gauge is generally aligned with an indicia marking on either the fixed angle drill guide or the variable angle drill guide feature to indicate an appropriate length of a bone anchor configured for anchoring within the bore in the bone.

30. A method, comprising:
providing a bone plate including a plurality of bone screw openings sized to receive bone screws;
providing a guide block including at least two drill guide passages extending therethrough, each of the drill guide passages having a conically-shaped inner guide surface;
selectively and removably engaging the guide block with the bone plate wherein the drill guide passages are substantially aligned with corresponding ones of the bone screw openings;
inserting a fixed angle drill guide including a distal portion having a conically-shaped outer guide surface within a selected one of the drill guide passages in the guide block and matingly engaging the conically-shaped outer guide surface with the conically-shaped inner guide surface of the selected drill guide passage to maintain orientation of the fixed angle drill guide at a predetermined fixed angular orientation relative to the guide block and the bone plate; and
inserting a variable angle drill guide including a distal portion within a selected one of the drill guide passages in the guide block, the distal portion of the variable angle drill guide having an outer guide surface sized smaller than the conically-shaped inner guide surface of the selected drill guide passage to permit orientation of the variable angle drill guide at a variable angular orientation relative to the guide block and the bone plate.

31. The method of claim 30 further comprising engaging a distal end of either of the drill guides within one of the bone screw openings in the bone plate that is substantially aligned with the selected drill guide passage in which the drill guide is positioned.

32. The method of claim 30 further comprising:
inserting a drill through either of the drill guides and forming a bore in the bone that is aligned with a corresponding one of the bone screw openings in the bone plate; and
passing a bone screw through the corresponding one of the bone screw openings in the bone plate and into the bone.

33. The method of claim 30 wherein a first of the drill guide passages in the guide block is arranged along a first axis; and
wherein a second of the drill guide passages in the guide block is arranged along a second axis that is not parallel with the first axis.

34. The method of claim 30 wherein the guide block has a first surface facing an upper surface of the bone plate when the guide block is selectively engaged with the bone plate;

wherein the guide block includes a second surface opposite the first surface; and wherein the conically-shaped inner guide surface of the drill guide passages extends from the second surface toward the first surface.

35. The method of claim 30 further comprising providing the bone plate, the guide block, the fixed angle drill guide, and the variable angle drill guide in a surgical kit.

* * * * *